United States Patent
Pavone et al.

(10) Patent No.: US 9,688,749 B2
(45) Date of Patent: *Jun. 27, 2017

(54) MOLECULES THAT ARE ABLE TO INHIBIT THE BINDING BETWEEN NGF AND THE TRKA RECEPTOR AS ANALGESICS WITH PROLONGED EFFECT

(75) Inventors: Flaminia Pavone, Rome (IT); Sara Martinelli, Rome (IT); Antonino Cattaneo, Rome (IT); Gabriele Ugolini, Rome (IT)

(73) Assignee: AbbVie Inc., North Chicago, IL (US)

( * ) Notice: Subject to any disclaimer, the term of this patent is extended or adjusted under 35 U.S.C. 154(b) by 2484 days.

This patent is subject to a terminal disclaimer.

(21) Appl. No.: 11/921,826

(22) PCT Filed: Jun. 7, 2006

(86) PCT No.: PCT/IT2006/000426
§ 371 (c)(1),
(2), (4) Date: Mar. 5, 2009

(87) PCT Pub. No.: WO2006/131951
PCT Pub. Date: Dec. 14, 2006

(65) Prior Publication Data
US 2009/0208490 A1 Aug. 20, 2009

(30) Foreign Application Priority Data
Jun. 7, 2005 (IT) .............. RM2005A0290

(51) Int. Cl.
*A61K 39/00* (2006.01)
*A61K 38/18* (2006.01)
*C07K 16/22* (2006.01)
*C07K 16/28* (2006.01)

(52) U.S. Cl.
CPC .......... *C07K 16/22* (2013.01); *C07K 16/2863* (2013.01); *A61K 2039/505* (2013.01); *C07K 2317/24* (2013.01); *C07K 2317/76* (2013.01)

(58) Field of Classification Search
CPC .............. A61K 2039/505; C07K 16/22; C07K 16/2863; C07K 2316/96; C07K 2317/24
USPC .................. 424/130.1, 133.1, 139.1
See application file for complete search history.

(56) References Cited

U.S. PATENT DOCUMENTS

| | | | |
|---|---|---|---|
| 4,230,691 A | 10/1980 | Young | |
| 5,147,294 A | 9/1992 | Smith et al. | |
| 5,639,641 A | 6/1997 | Pedersen et al. | |
| 5,693,761 A | 12/1997 | Queen et al. | |
| 5,747,060 A | 5/1998 | Sackler et al. | |
| 6,017,878 A | 1/2000 | Saragovi et al. | |
| 6,022,875 A | 2/2000 | Zimmer et al. | |
| 6,548,062 B2 | 4/2003 | Buchkovich et al. | |
| 6,881,719 B2 | 4/2005 | Saragovi et al. | |
| 6,919,426 B2 | 7/2005 | Boone et al. | |
| 7,252,822 B2 | 8/2007 | Shelton et al. | |
| 7,255,860 B2 | 8/2007 | Shelton et al. | |
| 7,371,559 B2 | 5/2008 | Boone et al. | |
| 7,425,329 B2 | 9/2008 | Shelton et al. | |
| 7,449,616 B2 | 11/2008 | Pons et al. | |
| 7,522,822 B2 | 4/2009 | Trujillo et al. | |
| 7,569,364 B2 | 8/2009 | Rosenthal et al. | |
| 7,601,818 B2 | 10/2009 | Wild, Jr. et al. | |
| 7,655,231 B2 | 2/2010 | Shelton et al. | |
| 7,655,232 B2 | 2/2010 | Pons et al. | |
| 7,727,527 B2 | 6/2010 | Shelton | |
| 7,795,413 B2 | 9/2010 | Wild, Jr. et al. | |
| 7,988,967 B2 | 8/2011 | MacDonald et al. | |
| 8,007,800 B2 | 8/2011 | Shelton et al. | |
| 8,257,710 B2 * | 9/2012 | Cattaneo et al. .......... 424/143.1 | |
| 2001/0046959 A1 | 11/2001 | Buchkovich et al. | |
| 2003/0087804 A1 | 5/2003 | Hempstead et al. | |
| 2004/0071701 A1 | 4/2004 | Delafoy et al. | |
| 2004/0131515 A1 | 7/2004 | Alexanian et al. | |
| 2004/0131615 A1 | 7/2004 | Shelton et al. | |
| 2004/0228862 A1 | 11/2004 | Shelton et al. | |
| 2004/0237124 A1 | 11/2004 | Pons et al. | |
| 2006/0147450 A1 | 7/2006 | Shelton | |
| 2007/0264195 A1 | 11/2007 | Nykiaer et al. | |
| 2008/0081040 A1 | 4/2008 | Shelton et al. | |
| 2008/0107658 A1 | 5/2008 | Franks et al. | |
| 2008/0213282 A1 | 9/2008 | Jacob et al. | |
| 2009/0155274 A1 | 6/2009 | Wild, Jr. et al. | |
| 2009/0300780 A1 | 12/2009 | Cattaneo et al. | |
| 2010/0034818 A1 | 2/2010 | Wild, Jr. et al. | |
| 2010/0055097 A1 | 3/2010 | Kaisheva et al. | |
| 2010/0111970 A1 | 5/2010 | Pons et al. | |

(Continued)

FOREIGN PATENT DOCUMENTS

EP 0578515 A3 1/1994
EP 0592106 B1 4/1994

(Continued)

OTHER PUBLICATIONS

Rudikoff et al., PNAS, vol. 79, 1982, pp. 1979-1983.*
Harrington, A.W. et al., "Secreted proNGF is a pathophysiological death-inducing ligand after adult CNS injury," PNAS, vol. 101(16):6226-6230 (2004).
Hasan, Wohaib et al., "Coordinate expression of NGF and alpha-smooth muscle actin mRNA and protein in cutaneous would tissue of developing and adult rats," Cell Tissue Res., vol. 300:97-109 (2000).
Field, Mark John et al., "Enadoline, a selective kappa-opioid receptor agonist shows potent antihyperalgesic and antiallodynic actions in a rat model of surgical pain," Pain, vol. 80:383-389 (1999).

(Continued)

*Primary Examiner* — Kimberly A. Ballard
*Assistant Examiner* — Stacy N MacFarlane
(74) *Attorney, Agent, or Firm* — McAndrews, Held & Malloy, Ltd.

(57) ABSTRACT

Use of an anti-NGF antibody capable of inhibiting the binding between NGF and TrkA, capable of blocking the biological activity of TrkA for the preparation of a medicament for treating and/or preventing chronic pain.

20 Claims, 6 Drawing Sheets

(56) References Cited

U.S. PATENT DOCUMENTS

Figure 1:
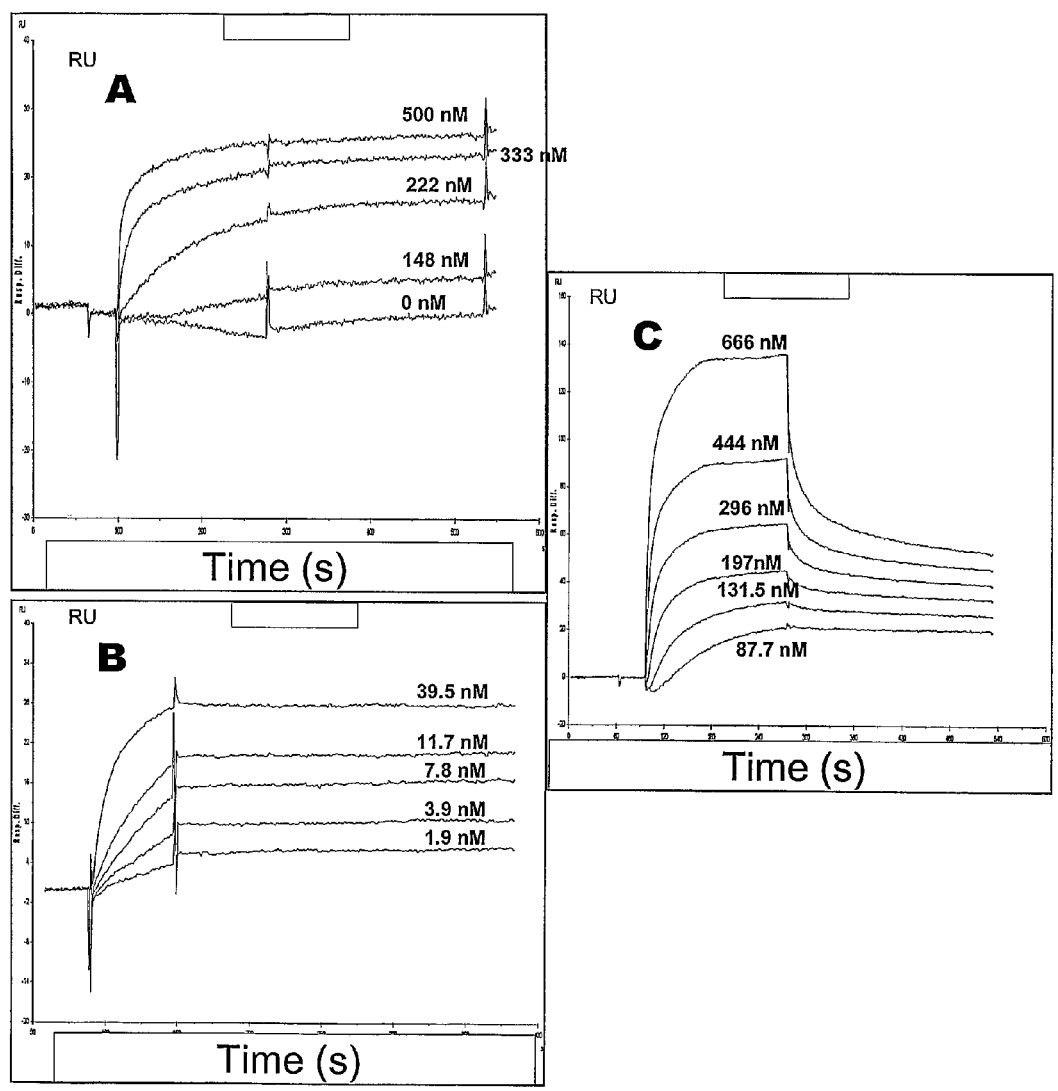

| | | |
|---|---|---|
| 2010/0143355 A1 | 6/2010 | Shelton et al. |
| 2010/0240582 A1 | 9/2010 | Boone et al. |
| 2010/0260775 A1 | 10/2010 | Mills et al. |
| 2010/0267934 A1 | 10/2010 | Van De Winkel et al. |
| 2011/0014208 A1 | 1/2011 | MacDonald et al. |
| 2011/0033447 A1 | 2/2011 | Rosenthal et al. |
| 2011/0091476 A1 | 4/2011 | Wild, Jr. et al. |
| 2011/0191872 A1 | 8/2011 | Cattaneo et al. |
| 2011/0243961 A1 | 10/2011 | Shelton et al. |
| 2011/0256587 A1 | 10/2011 | Macdonald et al. |

FOREIGN PATENT DOCUMENTS

| | | |
|---|---|---|
| EP | 1255824 B1 | 11/2002 |
| EP | 1401498 B1 | 3/2004 |
| EP | 1556083 B1 | 7/2005 |
| EP | 1575522 B1 | 9/2005 |
| EP | 1594441 B1 | 11/2005 |
| EP | 1732949 B1 | 12/2006 |
| EP | 1891966 A1 | 2/2008 |
| EP | 2100902 A1 | 9/2009 |
| EP | 2191846 A1 | 6/2010 |
| EP | 2206728 A1 | 7/2010 |
| EP | 2263692 A1 | 12/2010 |
| EP | 2270048 A2 | 1/2011 |
| WO | 90/10644 A1 | 9/1990 |
| WO | 92/08483 A1 | 5/1992 |
| WO | 92/09631 A1 | 6/1992 |
| WO | 92/22653 A1 | 12/1992 |
| WO | 93/06213 A1 | 4/1993 |
| WO | 93/16184 A1 | 8/1993 |
| WO | 00/37103 A2 | 6/2000 |
| WO | 00/73344 A2 | 12/2000 |
| WO | 01/10203 A2 | 2/2001 |
| WO | 01/64247 A2 | 9/2001 |
| WO | 01/70984 A2 | 9/2001 |
| WO | 01/78698 A2 | 10/2001 |
| WO | 02/096356 A2 | 12/2002 |
| WO | 02/096458 A1 | 12/2002 |
| WO | 02/100387 A1 | 12/2002 |
| WO | 2004/026329 A1 | 4/2004 |
| WO | 2004/032852 A2 | 4/2004 |
| WO | 2004/032870 A2 | 4/2004 |
| WO | 2004/056385 A2 | 7/2004 |
| WO | 2004/058184 A2 | 7/2004 |
| WO | 2004/065560 A2 | 8/2004 |
| WO | 2004/073653 A2 | 9/2004 |
| WO | 2011/096122 A2 | 11/2004 |
| WO | 2005/000194 A2 | 1/2005 |
| WO | 2005/019266 A2 | 3/2005 |
| WO | 2005/044293 A2 | 5/2005 |
| WO | 2005/061540 A2 | 7/2005 |
| WO | 2005/105847 A2 | 11/2005 |
| WO | 2005/111077 A2 | 11/2005 |
| WO | 2006/077441 A1 | 7/2006 |
| WO | 2006/110883 A2 | 10/2006 |
| WO | 2006/131951 A2 | 12/2006 |
| WO | 2006/131952 A1 | 12/2006 |
| WO | 2006/137106 A2 | 12/2006 |
| WO | 2008/079290 A2 | 7/2008 |
| WO | 2008/145142 A1 | 12/2008 |
| WO | 2009/023540 A1 | 2/2009 |
| WO | 2009/077993 A2 | 6/2009 |
| WO | 2011/116090 A1 | 9/2011 |

OTHER PUBLICATIONS

Hefti, Franz F. et al., "Novel class of pain drugs based on antagonism of NGF," Trends in Pharmacological Sciences, vol. 27(2):85-91 (2006).

Herzberg, Uri et al., "NGF involvement in pain induced by chronic constriction injury of the rat sciatic nerve," NeuroReport, vol. 8:1613-1618 (1997).

Hill, R.G., "Molecular Basis for the Perception of Pain," Neuroscientist, vol. 7(4):282-292 (2001).

Hongo, Jo-Anne S. et al., "Antibody Binding Regions on Human Nerve Growth Factor Identified by Homolog- and Alanine-Scanning Mutagenesis," Hybridoma, vol. 19(3):215-227 (2000).

Honore, Prisca et al., "Bone Cancer Pain: From Mechanisms to Model to Therapy," Pain Medicine, vol. 1(4):303-309 (2000).

Hurley, Robert W. et al., "Sex, Gender, and Pain: An Overview of a Complex Field," Anesthesia & Analgesia, vol. 107(1):309-317 (2008).

Ishikawa, Toshizo, "Involvement of Nerve Growth Factor in Development of Hyperalgesia," Jpn. Pharmacol. Ther., vol. 26(6):63-69 (1998).

Jaggar, S.I. et al., "Inflammation of the rat urinary bladder is associated with a referred thermal hyperalgesia which is nerve growth factor dependent," British Journal of Anaesthesia, vol. 83(3):442-448 (1999).

Ji, Ru-Rong et al., "p38 MAPK Activation by NGF in Primary Sensory Neurons after Inflammation Increases TRPV1 Levels and Maintains Heat Hyperalgesia," Neuron, vol. 36:57-68 (2002).

Jongen, J.L.M. et al., "Neurotrophic Factors and Cancer Pain: The Expression of NGF, GDNF and BDNF by the Murine Osteolytic Sarcoma Cell Line 2472 in Vitro and in Vivo and Their Potential Involvement in Bone Cancer Pain," Society for Neuroscience, Abstract No. 52.2 (2002).

Jongen, J.L.M. et al., "Neurotrophic factors and cancer pain: The expression of NGF, GDNF and BDNF by the murine osteolytic sarcoma cell line 2472 in vitro and in vivo and their potential involvement in bone cancer pain," Society for Neuroscience, Abstract No. 52.20 (2002).

Joranson, David E. et al., "Trends in Medical Use and Abuse of Opioid Analgesics," JAMA, vol. 283(13):1710-1714 (2000).

Kehlet, Henrik, "Synergism between Analgesics," Annals of Medicine, vol. 27:259-262 (1995).

Kessler, J.A., "Differential Regulation of Peptide and Catecholamine Characters in Cultured Sympathetic Neurons," Neuroscience, vol. 15(3):827-839 (1985).

Kessler, John A., "Parasympathetic, Sympathetic, and Sensory Interactions in the Iris: Nerve Growth Factor Regulates Cholinergic Ciliary Ganglion Innervation In Vivo," The Journal of Neuroscience, vol. 5(10):2719-2725 (1985).

Kidd, B.L. et al., "Mechanisms of inflammatory pain," British Journal of Anaesthesia, vol. 87(1):3-11 (2001).

Knusel, Beat et al., "K-252 Compounds: Modulators of Neurotrophin Signal Transduction," Journal of Neurochemistry, vol. 59(6):1987-1996 (1992).

Koltzenburg, Martin et al., "Neutralization and endogenous NGF prevents the sensitization of nociceptors supplying inflamed skin," European Journal of Neuroscience, vol. 11:1698-1704 (1999).

Labuz, Dominika et al., "Relative contribution of peripheral verus central opioid receptors to antinociception," Brain Research, vol. 1160:30-38 (2007).

Lamb, K. et al., "Nerve growth factor and gastric hyperalgesia in the rat," Neurogastroenterol Motil, vol. 15:355-361 (2003).

Leem, J.W. et al., "Anti-NGF Treatment Suppresses Abnormal Pain Behaviors Induced After Spinal Cord Injury in the Rat," (2000).

Lewin, Gary R. et al., "Nerve Growth Factor-induced Hyperalgesia in the Neonatal and Adult Rat," The Journal of Neuroscience, vol. 13(5):2136-2148 (1993).

Lewin, Gary R. et al., "Peripheral and Central Mechanisms of NGF-induced Hyperalgesia," European Journal of Neuroscience, vol. 6:1903-1912 (1994).

Lowe, E.M. et al., "Increased nerve growth factor levels in the urinary bladder of women with idiopathic sensory urgency and interstitial cystitis," British Journal of Urology, vol. 79:572-577 (1997).

Luger, Nancy M. et al., "Efficacy of systemic morphine suggests a fundamental difference in the mechanisms that generate bone cancer vs. inflammatory pain," Pain, vol. 99:397-406 (2002).

Mach, D.B. et al., "Sensory Nerves that Innervate Bone are Involved in Conveying Skeleton Pain," Society for Neuroscience, vol. 26:1960, Abstract No. 734.1 (2000).

(56) References Cited

OTHER PUBLICATIONS

MacPherson, Ross D., "The pharmacological basis of contemporary pain management," Pharmacology & Therapeutics, vol. 88:163-185 (2000).
Mantyh, Patrick W., "A mechanism-based understanding of bone cancer pain," Pathological Pain: From Molecular to Clinical Aspects: Novartis Foundation Symposium 261, vol. 261:194-219 (2004).
Mantyh, Patrick W. et al., "Molecular Mechanisms of Cancer Pain," Nature Reviews Cancer, vol. 2(3):201-209 (2002).
Matsuda, Hiroshi et al., "Role of Nerve Growth Factor in Cutaneous Wound Healing: Accelerating Effects in Normal and Healing-impaired Diabetic Mice," J. Exp. Med., vol. 187(3):297-306 (1998).
McGinty, Ann et al., "Cyclooxygenase-2 Expression Inhibits Trophic Withdrawal Apoptosis in Nerve Growth Factor-differentiated PC12 Cells," The Journal of Biological Chemistry, vol. 275(16):12095-12101 (2000).
McMahon, Stephen B., "NGF as a mediator of inflammatory pain," Phil. Trans. R. Soc. Lond. B, vol. 351:431-440 (1996).
McMahon, Stephen B. et al., "The biological effects of endogenous nerve growth factor on adult sensory neurons revealed by a trkA-IgG fusion molecule," Nature Medicine, vol. 1(8):774-780 (1995).
Millan, Mark J., "The Induction of Pain: An Integrative Review," Progress in Neurobiology, vol. 57:1-164 (1999).
Miller, Lauri J. et al., "Nerve Growth Factor and Chronic Prostatitis/Chronic Pelvic Pain Syndrome," Urology, vol. 59:603-608 (2002).
Mousa, Shaaban A. et al., "Nerve growth factor governs the enhanced ability of opioids to suppress inflammatory pain," Brain, vol. 130:502-513 (2007).
Nanduri, J. et al., "Immunological Determinants of Nerve Growth Factor Involved in p140trk (Trk) Receptor Binding," Journal of Neuroscience Research, vol. 37:433-444 (1994).
Nykjaer, Anders et al., "Sortilin is essential for proNGF-induced neuronal cell death," Nature, vol. 427:843-848 (2004).
Oddiah, Daniela et al., "Rapid increase of NGF, BDNF and NT-3 mRNAs in inflamed bladder," NeuroReport, vol. 9:1455-1458 (1998).
Omote, Keiichi et al., "The Effects of Peripheral Administration of a Novel Selective Antagonist for Prostaglandin E Receptor Subtype EP1, ONO-8711, in a Rat Model of Postoperative Pain," Anesth. Analg., vol. 92:233-238 (2001).
Onttonen, Tiina et al., "The Mechanical Antihyperalgesic Effect of Intrathecally Administered MPV-2426, a Novel alpha2-Adrenoceptor Agonist, in a Rat Model of Postoperative Pain," Anesthesiology, vol. 92:1740-1745 (2000).
Ossipov, Michael H. et al., "Spinal and Supraspinal Mechanisms of Neuropathic Pain," Annals of the New York Academy of Sciences, vol. 909:12-24 (2000).
Owolabi, Joshua B. et al., "Characterization of Antiallodynic Actions of ALE-0540, a Novel Nerve Growth Factor Receptor Antagonist, in the Rat," The Journal of Pharmacology and Experimental Therapeutics, vol. 289(3):1271-1276 (1999).
Peter, Elizabeth A. et al., "Ibuprofen versus acetaminophen with codeine for the relief of perineal pain after childbirth: a randomized controlled trial," CMAJ, vol. 165(9):1203-1209 (2001).
Pogatzki, Esther M. et al., "Characterization of Adelta- and C-Fibers Innervating the Plantar Rat Hindpaw One Day After an Incision," J. Neurophysiol., vol. 87:721-731 (2002).
Pogatzki, Esther M. et al., "Effect of Pretreatment with Intrathecal Excitatory Amino Acid Receptor Antagonists on the Development of Pain Behavior Caused by Plantar Incision," Anesthesiology, vol. 95:489-496 (2000).
Pogatzki-Zahn, Esther M. et al., "Postoperative pain-clinical implications of basic research," Best Practice & Research Clinical Anaesthesiology, vol. 21(1):3-13 (2007).
U.S. Appl. No. 10/583,618, filed Sep. 19, 2008, Antonino Cattaneo.
U.S. Appl. No. 12/837,996, filed Jul. 16, 2010, Antonino Cattaneo.
U.S. Appl. No. 12/838,034, filed Jul. 16, 2010, Antonino Cattaneo.
U.S. Appl. No. 12/838,062, filed Jul. 16, 2010, Antonino Cattaneo.
U.S. Appl. No. 12/773,488, filed May 4, 2010, John Powell.
U.S. Appl. No. 13/049,473, filed Mar. 16, 2011, Wolfgang Fraunhofer.
U.S. Appl. No. 10/583,618, filed Apr. 4, 2012, Suzanne Marie Noakes.
U.S. Appl. No. 10/583,618, filed Apr. 1, 2011, Suzanne Marie Noakes.
U.S. Appl. No. 10/583,618, filed Aug. 24, 2010, Suzanne Marie Noakes.
U.S. Appl. No. 10/583,618, filed Apr. 2, 2010, Shin Lin Chen.
U.S. Appl. No. 12/837,996, filed Sep. 13, 2011, Jon McClelland Lockard.
U.S. Appl. No. 12/838,034, filed Sep. 9, 2011, Jon McClelland Lockard.
U.S. Appl. No. 12/838,062, filed Oct. 12, 2011, Suzanne Marie Noakes.
Pogatzki, Esther M. et al., "Role of the Rostral Medial Medulla in the Development of Primary and Secondary Hyperalgesia after Incision in the Rat," Anesthesiology, vol. 96:1153-1160 (2002).
Premkumar, Louis S. et al., "Induction of vanilloid receptor channel activity by protein kinase C," Nature, vol. 408:985-990 (2000).
Przewlocki, Ryszard et al., "Opioids in chronic pain," European Journal of PHarmacology, vol. 429:79-91 (2001).
Queen, Cary et al., "A humanized antibody that binds to the interleukin 2 receptor," Proc. Natl. Acad. Sci. USA, vol. 86:10029-10033 (1989).
Ramer, Matt S. et al., "Adrenergic innervation of rat sensory ganglia following proximal or distal painful sciatic neuropathy: distinct mechanisms revealed by anti-NGF treatment," European Journal of Neuroscience, vol. 11:837-846 (1999).
Ramer, Matt S. et al., "Nerve growth factor induces P2X3 expression in sensory neurons," Journal of Neurochemistry, vol. 77:864-875 (2001).
Ramsland, Paul A. et al., "Crystal structures of human antibodies: a detailed and unfinished tapestry of immunoglobulin gene products," J. Mol. Recognit., vol. 15:248-259 (2002).
Reeh, Peter W. et al., "Nociceptor excitation by thermal sensitization—a hypothesis," Progress in Brain Research, vol. 129:39-50 (2000).
Ro, Long-Sun et al., "Effect of NGF and anti-NGF on neuropathic pain in rats following chronic constriction injury of the sciatic nerve," Pain, vol. 79:265-274 (1999).
Ruberti, Francesca et al., "Cloning and Expression of an Anti-Nerve Growth Factor (NGF) Antibody for Studies Using the Neuroantibody Approach," Cellular and Molecular Neurobiology, vol. 13(5):559-568 (1993).
Ruberti, Frencesca et al., "The use of the RACE method to clone hybridoma cDNA when V region primers fail," Journal of Immunological Methods, vol. 173:33-39 (1994).
Rudikoff, Stuart et al., "Single amino acid substitution altering antigen-binding specificity," Proc. Natl. Acad. Sci. USA, vol. 79:1979-1983 (1982).
Rueff, Alain et al., "Characteristics of nerve growth factor induced hyperalgesia in adult rats: dependence on enhanced bradykinin-1 receptor activity but not neurokinin-1 receptor activation," Pain, vol. 66: 359-372 (1996).
Rueff, Alain et al., "Nerve Growth Factor nad NT-5 Induce Increased Thermal Sensitivity of Cutaneous Nociceptors In Vitro," Journal of Neurophysiology, vol. 76(5):3593-3596 (1996).
Sabino, M.C. et al., "Defining the Cellular and Molecular Mechanisms that Generate and Maintain Bone Cancer Pain," Society for Neuroscience, vol. 27:143, Abstract No. 55.3 (2001).
Sabino, Mary Ann C. et al., "Different Tumors in Bone Each Give Rise to a Distinct Pattern of Skeletal Destruction, Bone Cancer-Related Pain Behaviors and Neurochemical Changes in the Central Nervous System," Int. J. Cancer, vol. 104:550-558 (2003).
Safieh-Garabedian, Bared et al., "Contribution of interleukin-1beta to the inflammation-induced increase in nerve growth factor levels and inflammatory hyperalgesia," British Journal of Pharmacology, vol. 115:1265-1275 (1995).
Safieh-Garabedian, Bared et al., "Involvement of Interleukin-1beta, Nerve Growth Factor, and Prostaglandin-E2 in the Hyperalgesia Induced by Intraplantar Injections of Low Doses of Thymulin," Brain, Behavior, and Immunity, vol. 11:185-200 (1997).

(56) References Cited

OTHER PUBLICATIONS

Safieh-Garabedian, B. et al., "The role of cytokines and prostaglandin-E2 in thymulin induced hyperalgesia," Neuropharmacology, vol. 39:1653-1661 (2000).
Sammons, Melanie J. et al., "Carrageenan-induced thermal hyperalgesia in the mouse: role of nerve growth factor and the mitogen-activated protein kinase pathway," Brain Research, vol. 876:48-54 (2000).
Sarchielli, Paola et al., "Levels of nerve growth factor in cerebrospinal fluid of chronic daily headache patients," Neurology, vol. 57(1):132-134 (2001).
Schwei, Matthew J. et al., "Neurochemical and Cellular Reorganization of the Spinal Cord in a Murine Model of Bone Cancer Pain," The Journal of Neuroscience, vol. 19(24):10886-10897 (1999).
Sedel, Frederic et al., "Nerve growth factor (NGF) induces motoneuron apoptosis in rat embryonic spinal cord in vitro," European Journal of Neuroscience, vol. 11:3904-3912 (1999).
Shelton, David L. et al., "Expression of the beta-nerve growth factor gene correlates with the density of sympathetic innervation in effector organs," Proc. Natl. Acad. Sci. USA, vol. 81:7951-7955 (1984).
Shelton, David L. et al., "Neurotrophins and neurotrophin and antagonists as potential therapeutics," Restorative Neurology and Neuroscience, vol. 8:99-100 (1995).
Shu, X.-Q. et al., "Neurotrophins and hyperalgesia," Proc. Natl. Acad. Sci. USA, vol. 96:7693-7696 (1999).
Sorkin, Linda S. et al., "Acute Pain Mechanisms," Surgical Clinics of North America, vol. 79(2):213-229 (1999).
Stein, Christoph et al., "Peripheral mechanisms of opioid analgesia," Current Opinion in Pharmacology, vol. 9:3-8 (2009).
Stubhaug, A. et al., "Mapping of punctuate hyperalgesia around a surgical incision demonstrates that ketamine is a powerful suppressor of central sensitization to pain following surgery," Acta Anaesthesiol. Scand., vol. 41:1124-1132 (1997).
Svensson, Peter et al., "Injection of nerve growth factor into human masseter muscle evokes long-lasting mechanical allodynia and hyperalgesia," Pain, vol. 104:241-247 (2003).
Taglialatela, G. et al., "Nerve Growth Factor Modulates the Activation of the Hypothalamo-Pituitary-Adrenocortical Axis during the Stress Response," Endocrinology, vol. 129(4):2212-2218 (1991).
Tal, Michael et al., "Local injection of nerve growth factor (NGF) triggers degranulation of mast cells in rat paw," Neuroscience Letters, vol. 221:129-132 (1997).
Tallarida, Ronald J., "An Overview of Drug Combination Analysis with Isobolograms," The Journal of Pharmacology and Experimental Therapeutics, vol. 319(1):1-7 (2006).
Tamura, Midori et al., "Structural Correlates of an Anticarcinoma Antibody: Identification of Specificity-Determining Residues (SDRs) and Development of a Minimally Immunogenic Antibody Variant by Retention of SDRs Only," The Journal of Immunology, vol. 164:1432-1441 (2000).
Theodosiou, M. et al., "Hyperalgesia due to nerve damage: role of nerve growth factor," Pain, vol. 81:245-255 (1999).
Treede, Rolf-Detlef et al., "Peripheral and Central Mechanisms of Cutaneous Hyperalgesia," Progress in Neurobiology, vol. 38:397-421 (1992).
Tsuda, Makoto et al., "Role of endogenous ATP at the incision area in a rat model of postoperative pain," NeuroReport, vol. 12(8):1701-1704 (2001).
Urch, C.E. et al., "Alterations in dorsal horn neurones in a rat model of cancer-induced bone pain," Pain, vol. 106:347-356 (2003).
Wang, Yong-Xiang et al., "Effects of intrathecal administration of ziconotide, a selective neuronal N-type calcium channel blocker, on mechanical allodynia and heat hyperalgesia in a rat model of postoperative pain," Pain, vol. 84:151-158 (2000).
Wilder-Smith, Oliver H.G., "Pre-emptive analgesia and surgical pain," Progress in Brain Research, vol. 129:505-524 (2000).
Winston, John H. et al., "Acute Pancreatitis Results in Referred Mechanical Hypersensitivity and Neuropeptide Up-Regulation That Can Be Suppressed by the Protein Kinase Inhibitor K252a," The Journal of Pain, vol. 4(6):329-337 (2003).
Winston, John et al., "Nerve growth factor regulates VR-1 mRNA levels in cultures of adult dorsal root ganglion neurons," Pain, vol. 89:181-186 (2001).
Woolf, C.J. et al., "Nerve Growth Factor Contributes to the Generation of Inflammatory Sensory Hypersensitivity," Neuroscience, vol. 62(2):327-331 (1994).
Woolf, Clifford J. et al., "Neuronal Plasticity: Increasing the Gain in Pain," Science, vol. 288:1765-1768 (2000).
Woolf, Clifford J., "Phenotype modification of primary sensory neurons: the role of nerve growth factor in the production of persistent pain," Phil. Trans. R. Soc. Lond. B, vol. 351:441-448 (1996).
Woolf, Clifford J. et al., "Preemptive Analgesia—Treating Postoperative Pain by Preventing the Establishment of Central Sensitization," Anesth. Analg., vol. 77(2):362-379 (1993).
Xanthos, Dimitris N. et al., "The roles of nerve growth factor and cholecystokinin in the enhancement of morphine analgesia in a rodent model of central nervous system inflammation," Neuropharmacology, vol. 56:684-691 (2009).
Yamamoto, Tatsuo et al., "Anti-allodynic effects of oral COX-2 selective inhibitor on postoperative pain in the rat," Can. J. Anesth., vol. 47(4):354-360 (2000).
Yamamoto, Tatsuo et al., "Spinal N-acetyl-alpha-linked acidic dipeptidase (NAALADase) inhibition attenuates mechanical allodynia induced by paw carrageenan injection in the rat," Brain Research, vol. 909:138-144 (2001).
Yamdeu, Reine-Solange et al., "p38 Mitogen-activated Protein Kinase Activation by Nerve Growth Factor in Primary Sensory Neurons Upregulates Mu-Opioid Receptors to Enhance Opioid Responsiveness Toward Better Pain Control," Anesthesiology, vol. 114(1):150-161 (2011).
Zahn, Peter K. et al., "Effect of Blockade of Nerve Growth Factor and Tumor Necrosis Factor on Pain Behaviors After Plantar Incision," The Journal of Pain, vol. 5(3):157-163 (2004).
Zahn, Peter K. et al., "Effect of Systemic and Intrathecal Morphine in a Rat Model of Postoperative Pain," Anesthesiology, vol. 86:1066-1077 (1997).
Zahn, Peter K. et al., "Intrathecal non-NMDA excitatory amino acid receptor antagonists inhibit pain behaviors in a rat model of postoperative pain," Pain, vol. 74:213-223 (1998).
Zahn, Peter K. et al., "Lack of Effect of Intrathecally Administered N-methyl-D-aspartate Receptor Antagonists in a Rat Model for Postoperative Pain," Anesthesiology, vol. 88:143-156 (1998).
Zahn, Peter K. et al., "Mechanisms for Pain Caused by Incisions," Regional Anesthesia and Pain Medicine, vol. 27(5):514-516 (2002).
Zahn, Peter K. et al., "Primary and Secondary Hyperalgesia in a Rat Model for Human Postoperative Pain," Anesthesiology, vol. 90:863-872 (1999).
International Search Report and Written Opinion for Application No. PCT/US2011/028659, pp. 1-12, dated Jul. 26, 2011.
European Office Action for Application No. 06756317.1, 14 pages, dated Mar. 16, 2012.
Database PDB [Online] Crystal Structure of Anti-NGF AD11 FAB Apr. 6, 2005 XP002402549, retrieved from EBI accession No. PDB:1ZAN_L.
European Extended Search Report in EP 11188102.5-2406 / 2484380, dated Jul. 11, 2012.
Wiesmann C et al., "Crystal structure of nerve growth factor in complex with the ligand-binding domain of the TrkA receptor," Nature, 401(6749):184-188 (1999) XP002961394.
Gonfloni, Stefania, "Recombinant antibodies as structural probes for neurotrophins", ISAS—International School for Advanced Studies, Trieste, Via Beirut 2-4, Dec. 1995.
Bennett, Gary J., et al., "A peripheral mononeuropathy in rat that produces disorders of pain sensation like those seen in man", Pain, 33 (1988) 87-107, Elsevier.
Berardi, N., et al., "Monoclonal antibodies to nerve growth factor affect the postnatal development of the visual system", Proc. Natl. Acad. Sc. USA, vol. 91, pp. 684-688, Jan. 1994, Neurobiology.

(56) References Cited

OTHER PUBLICATIONS

Bolt, Sarah, et al., "The generation of a humanized, non-mitogenic CD3 monoclonal antibody which retains in vitro immunosuppressive properties", Eur. J. Immunol. 1993, 23: 403-411.

Burnstock, Geoffrey, "Purine-mediated signalling in pain and visceral perception", Trends in Pharmacological Sciences, vol. 22 No. 4, Apr. 2001, pp. 182-188, Elsevier.

Capsoni, Simona, et al., "Alzheimer-like neurodegeneration in aged antinerve growth factor transgenic mice", PNAS, Jun. 6, 2000, vol. 97, No. 12, 6826-6831.

Cattaneo, Antonino, et al., "Functional Blockade of Tyrosine Kinase A in the Rat Basal Forebrain by a Novel Antagonistic Anti-Receptor Monoclonal Antibody", The Journal of Neuroscience, Nov. 15, 1999, 19(22):9687-9697, Society for Neuroscience.

Chuang, Hual-hu, "Bradykinin and nerve growth factor release the capsaicin receptor from PtdIns(4,5)P2-mediated inhibition", Nature, vol. 411, Jun. 21, 2001, pp. 957-962, Macmillan Magazines Ltd.

Covaceuszach, Sonia, et al., "Purification, crystallization, X-ray diffraction analysis and phasing of a Fab fragment of monocloncal neuroantibody aD11 against nerve growth factor", Acta Cryst. (2004), D60, 1323-1327, Issn. 0907-4449, Intl. Union of Crystallography.

Covaceuszach, Sonia, et al., "Purification, Crystallization and preliminary X-ray analysis of the Fab fragment from MNAC13, a novel antagonistic anti-tyrosine kinase A receptor monoclonal antibody", Acta Cryst. (2001), D57, 1307-1309, Intl. Union of Crystallography.

Covaceuszach, Sonia, et al., "Neutralization of NGF-TrkA Receptor Interaction by the Novel Antagonistic Anti-TrkA Monoclonal Antibody MNAC13: A Structural Insight", Proteins: Structure, Function, and Bioinformatics, 58:717-727 (2005), Wiley-Liss, Inc.

Djouhri, Laiche, "Time Course and Nerve Growth Factor Dependence of Inflammation-Induced Alterations in Electrophysiological Membrane Properties in Nociceptive Primary Afferent Neurons", The Journal of Neuroscience, Nov. 15, 2001, 21(22):8722-8733, Society for Neuroscience.

Frade, Jose Maria, et al., "Nerve growth factor: two receptors, multiple functions", BioEssays 20:137-145, 1998, John Wiley & Sons, Inc.

Galfre, G. et al., "Preparation of Monoclonal Antibodies: Strategies and Procedures", Methods in Enzymology, vol. 73, 1981, pp. 3-46, Academic Press Inc.

Harpf, Christoph, MD, et al., "Receptors for NGF and GDNF are Highly Expressed in Human Peripheral Nerve Neuroma", Muscle Nerve 25: 612-615, 2002, Wiley Periodicals, Inc.

Hempstead, Barbara L., "The many faces of p75NTR", Current Opinion in Neurobiology, 2002, 12:260-267, Elsevier Science Ltd.

Holtzman, David M. et al., "P140trk mRNA Marks NGF-Responsive Forebrain Neurons: Evidence that trk Gene Expression is Induced by NGF" Neuron, vol. 9, 465-478, Sep. 1992, Cell Press.

Horigome, Kazuhiko, "Mediator Release from Mast Cells by Nerve Growth Factor, Neurotrophin Specificity and Receptor Mediation", The Journal of Biological Chemistry, vol. 268, No. 20, Issue of Jul. 15, pp. 14881-14887, 1993, The Amer. Society for Biochemistry and Molecular Biology.

Hunt, Stephen P., "The Molecular Dynamics of Pain Control", Nature Reviews, Neuroscience, vol. 2, Feb. 2001, pp. 83-91, Macmillan Magazines Ltd.

Indo, Yasuhiro, "Molecular Basis of Congenital Insensitivity to Pain with Anhidrosis (CIPA): Mutations and Polymorphisms in TRKA (NTRK1) Gene Encoding the Receptor Tyrosine Kinase for Nerve Growth Factor", Human Mutation 18:462-471 (2001), Wiley-Liss Inc.

Indo, Yasuhiro, et al., "Mutations in the TRKA/NGF receptor gene in patients with congenital insensitivity to pain with anhidrosis", Nature Genetics, vol. 13 Aug. 1996, pp. 485-488, Nature Publishing Group.

Indo, Yasuhiro, et al., "Conogenital Insensitivity to Pain with Anhidrosis (CIPA): Novel Mutations of the TRKA (NTRK1) Gene, a Putative Uniparental Disomy, and a Linkage of the Mutant TRKA and PKLR Genes in a Family with CIPA and Pyruvate Kinase Deficiency", Human Mutation, 18:308-318, 2001, Wiley-Liss, Inc.

Julius, David, et al., "Molecular Mechanisms of Nociception", Nature, vol. 413, Sep. 13, 2001, pp. 203-210, Macmillan Magazines Ltd.

Kaplan, David R., "Studying signal transduction in neuronal cells: The Trk/NGF system", Progress in Brain Research, vol. 117, 1998, pp. 35-46, Elsevier Science BV.

Kawamoto, Keiko, et al., "Nerve Growth Factor Activates Mast Cells Through the Collaborative Interaction with Lysophosphatidylserine Expressed on the Membrane Surface of Activated Platelets", The Journal of Immunology, 2002, 168:6412-6419, The American Association of Immunologists, Inc.

Khakh, Baljit S., "Molecular Physiology of P2X Receptors and ATP Signalling at Synapses", Nature Reviews, vol. 2, Mar. 2001, 165, (2001), pp. 165-174, Macmillan Magazines Ltd.

Kryger, Gil S., et al., "Nerve Growth Factor Inhibition Prevents Traumatic Neuroma Formation in the Rat", The Journal of Hand Surgery, 2001; 26A:635-644, American Society for Surgery of the Hand.

Lee, Ramee, et al., "Regulation of Cell Survival by Secreted Proneurotrophins", Science 294, pp. 1945-1948, (2001); DOI:10.1126/science. 1065057.

Levi-Montalcini, R. et al., "The nerve growth factor 35 years later", Science 237, pp. 1154-1162,d (1987); DOI: 10.1126/science. 3306916.

Levi-Montalcini, R., et al., "Nerve growth factor: from neurotrophin to neurokine", Trends Neurosci. (1996), vol. 19, No. 11, 514-520, Elsevier Science Ltd.

Levine, Jon D., "New Directions in Pain Research: Molecules to Maladies", Neuron, vol. 20, 649-654, Apr. 1998, Cell Press.

Molnar, Margherita, et al., "A critical period in the sensitivity of basal forebrain cholinergic neurones to NGF deprivation", Developmental Neuroscience, NeuroReport 8, 575-579 (1997), Rapid Science Publishers.

Molnar, Margherita, et al., "The effects of anti-nerve growth factor monoclonal antibodies of developing basal forebrain neurons are transient and reversible", European Journal of Neuroscience, vol. 10, pp. 3127-3140, 1998, European Neuroscience Assoc.

Morisset, Valerie, et al., "Possible mechanisms of cannabinoid-induced antinociception in the spinal cord", European Journal of Pharmacology 429 (2001) 93-100, Elsevier Science B.V.

Nakatsuka, Terumasa, et al., "Activation of Central Terminal Vanilloid Receptor-1 Receptors and aβ-Methylene-ATP-Sensitive P2X Receptors Reveals a Converged Synaptic Activity onto the Deep Dorsal Horn Neurons of the Spinal Cord", The Journal of Neuroscience, Feb. 15, 2002, 22(4):1228-1237, Society for Neuroscience.

Nilsson, Gunnar, et al., "Human mast cells express functional TrkA and are a source of nerve growth factor", Eur. J. Immunol. 1997, 27:2295-2301, Wiley-VCH.

Porro, Carlo A., et al., "Spatial and Temporal Aspects of Spinal Cord and Brainstem Activation in the Formalin Pain Model", Progress in Neurobiology, vol. 41, pp. 565-607, 1993, Pergamon Press Ltd.

Pesavento, Emanuele, et al., "Blocking the NGF-TrkA Interaction Rescues the Developmental Loss of LTP in the Rat Visual Cortex: Role of the Cholinergic System", Neuron, vol. 25, 165-175, Jan. 2000, Cell Press.

Ruberti, Francesca, "Phenotypic Knockout of Nerve Growth Factor in Adult Transgenic Mice Reveals Severe Deficits in Basal Forebrain Cholinergic Neurons, Cell Death in the Spleen, and Skeletal Muscle Dystrophy", The Journal of Neuroscience, Apr. 1, 2000, 20(7):2589-2601, Society for Neuroscience.

Saper, Clifford B., et al., "Neuronal pathology in the nucleus basalis and associated cell groups in senile dementia of the Alzheimer's type: Possible role in cell loss", Neurology, 1985;35;1089-1095, American Academy of Neurology.

Saragovi, H. Uri, et al., "Development of pharmacological agents for targeting neurotrophins and their receptors", TiPS, Mar. 2000, vol. 21, pp. 93-98, Elsevier Science Ltd.

Sevcik, Molly A., et al., "Anti-NGF therapy profoundly reduces bone cancer pain and the accompanying increase in markers of peripheral and central sensitization", Pain 115 (2005), 128-141, Elsevier B.V.

(56) References Cited

OTHER PUBLICATIONS

Shu, Xiaoquan, et al., "Nerve growth factor acutely sensitizes the response of adult rat sensory neurons to capsaicin", Neuroscience Letters, 274 (1999), 159-162, Elsevier Science Ireland Ltd.
Sivilotti, Lucia, et al., "GABA Receptors Mechanisms in the Central Nervous System", Progress in Neurobiology, vol. 36, pp. 35-92, 1991, Pergamon Press.
Woolf, Clifford J., et al., "Peripheral Cell Types Contributing to the Hyperalgesic Action of Nerve Growth Factor in Inflammation", The Journal of Neuroscience, Apr. 15, 1996, 16(8):2716-2723, Society for Neuroscience.
Zhu, Zhaowen, et al., "Nerve Growth Factor Expression Correlates with Perineural Invasion and Pain in Human Pancreatic Cancer", Journal of Clinical Oncology, vol. 17, No. 8 Aug. 1999: pp. 2419-2428, American Society of Clinical Oncology.
Australian Government, Patent Examination Report No. 1, in Application No. 2012201465, dated Mar. 15, 2013.
Japanese Patent Office, Office action in JP2014-163809 dated Jul. 13, 2015.
Communication issued by the Examining Division Mar. 27, 2015, in European application 06756317.1.
Gonfloni, Ph.D. thesis entitled "Recombinant antibodies as structural probes for neutrophins," dated Dec. 1995.
Third Party Observations submitted Nov. 26, 2014, in European application 06756317.1.
Abram, Stephen E., "Necessity for an Animal Model of Postoperative Pain," Anesthesiology, vol. 86(5):1015-1017 (1997).
Accession No. C36005 (1996).
Accession No. Q9UL72 (2006).
Accession No. AAR22755 (2004).
Accession No. AAR53345 (2003).
Aloe, Luigi et al., "Nerve Growth Factor in the Synovial Fluid of Patients with Chronic Arthritis," Arthritis and Rheumatism, vol. 35(3):351-355 (1992).
Amann, R. et al., "Inhibition of carrageenan-induced edema by indomethacin or sodium salicylate does not prevent the increase of nerve growth factor in the rat hind paw," Neuroscience Letters, vol. 278:173-176 (2000).
Amann, Rainer et al., "Intraplantar injection of nerve growth factor into the rat hind paw: local edema and effects on thermal nociceptive threshold," Pain, vol. 64:323-329 (1995).
Amico-Roxas, M. et al., "Nerve Growth Factor Inhibits Some Acute Experimental Inflammations," Arch. Int. PHarmacodyn. Ther., vol. 299:269-285 (1989).
Angal, S. et al., "A Single Amino Acid Substitution Abolishes the Heterogeneity of Chimeric Mouse/Human (IgG4) Antibody," Molecular Immunology, vol. 30(1):105-108 (1993).
Averill, S. et al., "Immunocytochemical Localization of trkA Receptors in Chemically Identified Subgroups of Adult Rat Sensory Neurons," European Journal of Neuroscience, vol. 7:1484-1494 (1995).
Banik, R.K. et al., "Anti-NGF Treatment Attenuates Spontaneous Pain and Thermal, But Not Mechanical Hyperalgesia, After Hind Paw Incision in the Rat," Society for Neuroscience, Program No. 909.12 (2003).
Banik, R.K. et al., "Anti-NGF treatment attenuates spontaneous pain and thermal, but not mechanical hyperalgesia, after hind paw incision in the rat," Presentation No. 909-12, Neuroscience (2003).
Banik, Ratan K. et al., "Increased nerve growth factor after rat plantar incision contributes to guarding behavior and heat hyperalgesia," Pain, vol. 117:68-76 (2005).
Beattie, Michael S. et al., "ProNGF Induces p75-Mediates Death of Oligodendrocytes following Spinal Cord Injury," Neuron, vol. 36(3):375-386 (2002).
Bennett, David L.H. et al., "Endogenous nerve growth factor regulates the sensitivity of nociceptors in the adult rat," European Journal of Neuroscience, vol. 10:1282-1291 (1998).
Brennan, Timothy J. et al., "Characterization of a rat model of incisional pain," Pain, vol. 64:493-501 (1996).
Brennan, Timothy J. et al., "Comparison of Pre- versus Post-incision Administration of Intrathecal Bupivacaine and Intrathecal Morphine in a Rat Model of Postoperative Pain," Anesthesiology, vol. 87:1517-1528 (1997).
Brennan, Timothy J., "Postoperative Models of Nociception," ILAR J., vol. 40(3):129-136 (1999).
Brennan, T.J. et al., "Role of Nerve Growth Factor in a Rat Model for Postoperative Pain," Society for Neuroscience, vol. 24:880, Abstract No. 349.4 (1998).
Cahill, Catherine M. et al., "Intrathecal nerve growth factor restores opioid effectiveness in an animal model of neuropathic pain," Neuropharmacology, vol. 45:543-552 (2003).
Cain, Daivd M. et al., "Functional Interations between Tumor and Peripheral Nerve: Changes in Excitability and Morphology of Primary Afferent Fibers in a Murine Model of Cancer Pain," The Journal of Neuroscience, vol. 21(23):9367-9376 (2001).
Capsoni, Simona et al., "Muscular Dystrophy in Adult and Aged Anti-NGF Transgenic Mice Resembles an Inclusion Body Myopathy," Journal of Neuroscience Research, vol. 59:553-560 (2000).
Cattaneo, Antonino et al., "Three Distinct Types of Monoclonal Antibodies After Long-Term Immunization of Rats with Mouse Nerve Growth Factor," Journal of Neurochemistry, vol. 50:1003-1010 (1988).
Clohisy, Denis R. et al., "Bone Cancer Pain," Cancer, vol. 97(3 Suppl.):866-873 (2003).
Cohen, Stanley et al., "Purification and Properties of a Nerve Growth-promoting Factor Isolated from Mouse Sarcoma 180," Cancer Research, vol. 17(1):15-20 (1957).
Constantinou, Jason et al., "Nerve growth factor levels in developing rat skin: upregulation following skin wounding," NeuroReport, vol. 5:2281-2284 (1994).
Costigan, Michael et al., "Pain: Molecular Mechanisms," The Journal of Pain, vol. 1(3), Suppl. 1:35-44 (2000).
Covaceuszach, Sonia et al., "Dissecting NGF Interactions with TrkA and p75 Receptors by Structural and Functional Studies of an Anti-NGF Neutralizing Antibody," J. Mol. Biol., vol. 381:881-896 (2008).
De Craen, Anton J.M. et al., "Analgesic efficacy and safety of paracetamol-codeine combinations versus paracetamol alone: a systematic review," BMJ, vol. 313(7053):321-325 (1996).
Delafoy, Laure et al., "Role of nerve growth factor in the trinitrobenzene sulfonic acid-induced colonic hypersensitivity," Pain, vol. 105:489-497 (2003).
Diamond, Jack et al., "Sensory Nerves in Adult Rats Regenerate and Restore Sensory Function to the Skin Independently of Endogenous NGF," The Journal of Neuroscience, vol. 12(4):1467-1476 (1992).
Dirig, David M. et al., "Characterization of veriables defining hindpaw withdrawal latency evoked by radiant thermal stimuli," Journal of Neuroscience Methods, vol. 76:183-191 (1997).
Dmitrieva, Natalia et al., "Sensitisation of visceral afferents by nerve growth factor in the adult rat," Pain, vol. 66:87-97 (1996).
Durham, Paul L. et al., "Stimulation of the Calcitonin Gene-Related Peptide Enhancer by Mitogen-Activated Protein Kinases and Repression by an Antimigraine Drug in Trigeminal Ganglia Neurons," The Journal of Neuroscience, vol. 23(3):807-815 (2003).
Dyck, P.J. et al., "Intradermal recombinant human nerve growth factor induces pressure allodynia and lowered heat-pain threshold in humans," Neurology, vol. 48:501-505 (1997).
Fairbanks, Carolyn A. et al., "Spinal Plasticity of Acute Opioid Tolerance," J. Biomed. Sci., vol. 7:200-212 (2000).
Field, Mark J. et al., "Evaluation of Gabapentin and S-(+)-3-Isobutylgaba in a Rat Model of Postoperative Pain," The Journal of Pharmacology and Experimental Therapeutics, vol. 282(3):1242-1246 (1997).
Friedman, W.J. et al., "Regulation of Beta-Nerve Growth Factor Expression by Inflammatory Mediators in Hippocampal Cultures," Journal of Neuroscience Research, vol. 27:374-382 (1990).
Garaci, Enrico et al., "Anti-nerve growth factor Ab abrogates macrophage-mediated HIV-1 infection and depletion of CD4+ T lymphocytes in hu-SCID mice," PNAS, vol. 100(15):8927-8932 (2003).

(56) References Cited

OTHER PUBLICATIONS

Ghilardi, J.R. et al., "A Neuropathic Component to Bone Cancer Pain," Society for Neuroscience, Program No. 815.9 (2003).
Goldstein, Frederick J., "Adjuncts to opioid therapy," JAOA, vol. 102(9), Suppl. 3:S15-S20 (2002).
Gonzalez, M. Isabel et al., "Evaluation of PD 154075, a tachykinin NK1 receptor antagonist, in a rat model of postoperative pain," European Journal of Pharmacology, vol. 344:115-120 (1998).
Grabovsky, Yury et al., "Isobolographic Analysis for Combinations of a Full and Partial Agonist: Curved Isoboles," The Journal of Pharmacology and Experimental Therapeutics, vol. 310(3):981-986 (2004).
Grills, Brian L. et al., "Immunohistochemical localization of nerve growth factor in fractured and unfractured rat bone," Acta Orthop Scand, vol. 69(4):415-419 (1998).
Gwak, Young Seob et al., "Attenuation of mechanical hyperalgesia following spinal cord injury by administration of antibodies to nerve growth factor in the rat," Neuroscience Letters, vol. 336:117-120 (2003).
Halliday, Dale A. et al., "Elevated Nerve Growth Factor Levels in the Synovial Fluid of Patients with Inflammatory Joint Disease," Neurochemical Research, vol. 23(6):919-922 (1998).
Halvorson, Kyle G. et al., "A Blocking Antibody to Nerve Growth Factor Attenuates Skeletal Pain Induced by Prostate Tumor Cells Growing in Bone," Cancer Res., vol. 65(20):9426-9435 (2005).
Hamalainen, Minna M. et al., "Acute Effect of an Incision on Mechanosensitive Afferents in the Plantar Rat Hindpaw," J. Neurophysiol., vol. 87:712-720 (2002).
Hanks, G.W., "Opioid-responsive and opioid-non-responsive pain in cancer," British Medical Bulletin, vol. 47(3):718-731 (1991).

\* cited by examiner

SEQUENCE LISTING

<160> NUMBER OF SEQ ID NOS: 10

<210> SEQ ID NO 1
<211> LENGTH: 107
<212> TYPE: PRT
<213> ORGANISM: Artificial Sequence
<220> FEATURE:
<223> OTHER INFORMATION: synthetic peptide antibody light chain variable region

<400> SEQUENCE: 1

```
Asp Ile Gln Met Thr Gln Ser Pro Ala Ser Leu Ser Ala Ser Leu Gly
 1               5                  10                  15

Glu Thr Val Thr Ile Glu Cys Arg Ala Ser Glu Asp Ile Tyr Asn Ala
            20                  25                  30

Leu Ala Trp Tyr Gln Gln Lys Pro Gly Lys Ser Pro Gln Leu Leu Ile
        35                  40                  45

Tyr Asn Thr Asp Thr Leu His Thr Gly Val Pro Ser Arg Phe Ser Gly
 50                  55                  60

Ser Gly Ser Gly Thr Gln Tyr Ser Leu Lys Ile Asn Ser Leu Gln Ser
65                  70                  75                  80

Glu Asp Val Ala Ser Tyr Phe Cys Gln His Tyr Phe His Tyr Pro Arg
                85                  90                  95

Thr Phe Gly Gly Gly Thr Lys Leu Glu Leu Lys
            100                 105
```

<210> SEQ ID NO 2
<211> LENGTH: 122
<212> TYPE: PRT
<213> ORGANISM: Artificial Sequence
<220> FEATURE:
<223> OTHER INFORMATION: synthetic peptide antibody heavy chain variable region

<400> SEQUENCE: 2

```
Gln Val Gln Leu Lys Glu Ser Gly Pro Gly Leu Val Gln Pro Ser Gln
 1               5                  10                  15

Thr Leu Ser Leu Thr Cys Thr Val Ser Gly Phe Ser Leu Thr Asn Asn
            20                  25                  30

Asn Val Asn Trp Val Arg Gln Ala Thr Gly Arg Gly Leu Glu Trp Met
        35                  40                  45

Gly Gly Val Trp Ala Gly Gly Ala Thr Asp Tyr Asn Ser Ala Leu Lys
 50                  55                  60

Ser Arg Leu Thr Ile Thr Arg Asp Thr Ser Lys Ser Gln Val Phe Leu
65                  70                  75                  80

Lys Met His Ser Leu Gln Ser Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Thr Val Thr Val Ser Ala
        115                 120
```

<210> SEQ ID NO 3
<211> LENGTH: 107
<212> TYPE: PRT
<213> ORGANISM: Artificial Sequence
<220> FEATURE:
<223> OTHER INFORMATION: synthetic peptide variable region of the light chain of Hu-alpha D11

<400> SEQUENCE: 3

-continued

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Thr Asp Thr Leu His Thr Gly Val Pro Ser Arg Phe Ser Gly
    50                  55                  60

Ser Gly Ser Gly Thr Asp Tyr Thr Leu Thr Ile Ser Ser Leu Gln Pro
65              70                  75                  80

Glu Asp Phe Ala Thr Tyr Phe Cys Gln His Tyr Phe His Tyr Pro Arg
                85                  90                  95

Thr Phe Gly Gln Gly Thr Lys Val Glu Ile Lys
            100                 105

<210> SEQ ID NO 4
<211> LENGTH: 122
<212> TYPE: PRT
<213> ORGANISM: Artificial Sequence
<220> FEATURE:
<223> OTHER INFORMATION: synthetic peptide variable region of the heavy
      chain of Hu-alpha D11

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Asn
            20                  25                  30

Asn Val Asn Trp Val Arg Gln Ala Pro Gly Lys Gly Leu Glu Trp Val
        35                  40                  45

Gly Gly Val Trp Ala Gly Gly Ala Thr Asp Tyr Asn Ser Ala Leu Lys
    50                  55                  60

Ser Arg Phe Thr Ile Ser Arg Asp Asn Ser Lys Asn Thr Ala Tyr Leu
65              70                  75                  80

Gln Met Asn Ser Leu Arg Ala Glu Asp Thr Ala Val Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser
        115                 120

<210> SEQ ID NO 5
<211> LENGTH: 452
<212> TYPE: PRT
<213> ORGANISM: Artificial Sequence
<220> FEATURE:
<223> OTHER INFORMATION: synthetic peptide humanised anti-NGF

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Asn
            20                  25                  30

Asn Val Asn Trp Val Arg Gln Ala Pro Gly Lys Gly Leu Glu Trp Val
        35                  40                  45

Gly Gly Val Trp Ala Gly Gly Ala Thr Asp Tyr Asn Ser Ala Leu Lys
    50                  55                  60

Ser Arg Phe Thr Ile Ser Arg Asp Asn Ser Lys Asn Thr Ala Tyr Leu
 65                  70                  75                  80

Gln Met Asn Ser Leu Arg Ala Glu Asp Thr Ala Val Tyr Tyr Cys Ala
                 85                  90                  95

Arg Asp Gly Gly Tyr Ser Ser Thr Leu Tyr Ala Met Asp Ala Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
            450

<210> SEQ ID NO 6
<211> LENGTH: 452
<212> TYPE: PRT

<213> ORGANISM: Artificial Sequence
<220> FEATURE:
<223> OTHER INFORMATION: synthetic peptide humanised Hu-alpha D11

<400> SEQUENCE: 6

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Thr Asn Asn
            20                  25                  30

Asn Val Asn Trp Val Arg Gln Ala Pro Gly Lys Gly Leu Glu Trp Val
        35                  40                  45

Gly Gly Val Trp Ala Gly Gly Ala Thr Asp Tyr Asn Ser Ala Leu Lys
    50                  55                  60

Ser Arg Phe Thr Ile Ser Arg Asp Asn Ser Lys Asn Thr Ala Tyr Leu
65                  70                  75                  80

Gln Met Asn Ser Leu Arg Ala Glu Asp Thr Ala Val Tyr Tyr Cys Ala
                85                  90                  95

Arg Asp Gly Gly Tyr Ser Ser Thr Leu Tyr Ala Met Asp Ala Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Ala Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
```

```
Pro Val Leu Asp Ser Asp Gly Ser Phe Phe Leu Tyr Ser Lys Leu Thr
        385             390             395             400
                405                 410             415

Val Asp Lys Ser Arg Trp Gln Gln Gly Asn Val Phe Ser Cys Ser Val
                420             425                 430

Met His Glu Ala Leu His Asn His Tyr Thr Gln Lys Ser Leu Ser Leu
                435             440             445

Ser Pro Gly Lys
        450

<210> SEQ ID NO 7
<211> LENGTH: 449
<212> TYPE: PRT
<213> ORGANISM: Artificial Sequence
<220> FEATURE:
<223> OTHER INFORMATION: synthetic peptide humanised Hu-alpha D11

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Asn
            20                  25                  30

Asn Val Asn Trp Val Arg Gln Ala Pro Gly Lys Gly Leu Glu Trp Val
        35                  40                  45

Gly Gly Val Trp Ala Gly Gly Ala Thr Asp Tyr Asn Ser Ala Leu Lys
    50                  55                  60

Ser Arg Phe Thr Ile Ser Arg Asp Asn Ser Lys Asn Thr Ala Tyr Leu
65                  70                  75                  80

Gln Met Asn Ser Leu Arg Ala Glu Asp Thr Ala Val Tyr Tyr Cys Ala
                85                  90                  95

Arg Asp Gly Gly Tyr Ser Ser Thr Leu Tyr Ala Met Asp Ala Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Val Val Thr
            180                 185                 190

Val Pro Ser Ser Ser Leu Gly Thr Lys Thr Tyr Thr Cys Asn Val Asp
    195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
```

```
                290                 295                 300
Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Lys

<210> SEQ ID NO 8
<211> LENGTH: 214
<212> TYPE: PRT
<213> ORGANISM: Artificial Sequence
<220> FEATURE:
<223> OTHER INFORMATION: synthetic peptide Humanised Hu-alpha D11

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Asn Ala
                20                  25                  30

Leu Ala Trp Tyr Gln Gln Lys Pro Gly Lys Ala Pro Lys Leu Leu Ile
                35                  40                  45

Tyr Asn Thr Asp Thr Leu His Thr Gly Val Pro Ser Arg Phe Ser Gly
                50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln His Tyr Phe His Tyr Pro Arg
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205
```

```
Phe Asn Arg Gly Glu Cys
    210

<210> SEQ ID NO 9
<211> LENGTH: 9
<212> TYPE: PRT
<213> ORGANISM: Homo sapiens

<400> SEQUENCE: 9

Glu Val Asn Ile Asn Asn Ser Val Phe
1               5

<210> SEQ ID NO 10
<211> LENGTH: 13
<212> TYPE: PRT
<213> ORGANISM: Homo sapiens

<400> SEQUENCE: 10

Gly Asp Lys Thr Thr Ala Thr Asp Ile Lys Gly Lys Glu
1               5                   10
```

MOLECULES THAT ARE ABLE TO INHIBIT THE BINDING BETWEEN NGF AND THE TRKA RECEPTOR AS ANALGESICS WITH PROLONGED EFFECT

This application is the U.S. National Phase of, and Applicants claim priority from, International Application Number PCT/IT2006/000426 filed 7 Jun. 2006 and Italian Application bearing Serial No. RM 2005 A 00290 filed 7 Jun. 2005, which are incorporated herein by reference.

BACKGROUND TO THE INVENTION

The present invention relates to the use of molecules that are capable of inhibiting the binding between NGF and its receptor, TrkA. In particular, it relates to antibodies for one of the two molecules that, by blocking the biological activity of NGF, have a prolonged analgesic effect. Owing to the enduring analgesic effect thereof they are an advantageous therapy for pathologies with persistent forms of pain, known also as chronic pain, such as but not limited to neuropathic or oncological pain.

STATE OF THE ART

The nociceptive signals afferent to the spinal cord are carried by the fibres Aδ and C, the cell bodies of which (primary sensitive neurons) are located in the spinal dorsal ganglia (DRG). The primary sensitive neurons release glutamate together with ATP as an excitatory neurotransmitter, and various other substances such as substance P and CGRP (calcitonin-gene-related-peptide), (Hunt and Mantyh, 2001). The release of these excitatory neurotransmitters is controlled by various classes of receptors present on the afferent terminals, including those that are sensitive to capsaicin (vanilloid receptors, VR1), those activated by GABA, those activated by ATP itself and those activated by cannabinoids (CB1) (Sivilotti and Nistri, 1991; Hunt and Mantyh, 2001; Khakh, 2001; Morisset et al., 2001). One of the physiopathological mechanisms whereby chronic pain occurs is allodynia, i.e. the transformation of stimuli that are not normally painful into painful sensations. This phenomenon involves various ionic currents and thus various channels of the "ligand-gated" type, including the receptor for the capsaicin, VR1, and the ionotropic receptors for ATP (Khakh, 2001). The simultaneous activation of the receptors for VR1 and of those for ATP on spinal nociceptive interneurons generates a considerable accumulation of the excitatory synaptic signals with reinforcement of the transmission of the painful stimulus (Nakatsuka et al., 2002). On this basis, it is therefore clear that the ATP receptors (especially those belonging to the class P2X3) play a fundamental role in the pain paths (Burnstock, 2001). These receptors are present on the peripheral nerve terminals activated by algogenic stimuli, on the cell bodies of the neurons in the DRGs and on the presynaptic terminals thereof as well as naturally on postsynaptic terminals in the spinal cord (Khakh, 2001). There is considerable evidence that shows that the system constituted by the nerve growth factor (NGF) and by the high-affinity receptor thereof, TrkA (Levi-Montalcini, 1987; Levi-Montalcini et al., 1996; Frade and Barde, 1998; Kaplan, 1998) plays a fundamental role in the molecular processes underlying the main forms of "persistent" pain. This indicates a main therapeutical area (the one of pain, with particular reference to the "tonic" forms), for the antibodies that block the NGF/TrkA system (Levine, 1998). The development of sensitive nociceptive neurons depends greatly on NGF, and the responses of the adult nociceptors are modulated by the same factor (Julius and Basbaum, 2001). In particular, NGF exerts acute sensitisation of the capsaicin algogenic stimulus (Shu and Mendell, 1999). From a functional point of view, the nociceptive neurons, following chronic inflammation, develop alterations in the frequency and duration of their action potential. These phenomena regress by blocking endogenous NGF leading to a significant attenuation of the hyperexcitability that is typical of chronic painful states (Djouhri et al., 2001). NGF action in defining the pain threshold in adult nociceptors is mediated by the TrkA receptor, also through modulation of the response mediated by the VR1 receptor present on the nociceptive terminals. The TrkA-dependent potentiation of the VR1 response is thought to occur through the intracellular transduction pathway of the gamma version of phospholipase C (PLCgamma, Chuang et al, 2001). The levels of peripheral NGF are increased in inflammatory processes, while the administration of exogenous NGF has a hyperalgesic effect on rats and produces muscular pain in humans. Furthermore, NGF produces hypersensitisation to heat stimulation in humans and mammals in general. NGF is released by mastocytes, fibroblasts and other cell types in the peripheral sites where inflammatory processes occur. In particular the mastocytes appear to play a fundamental role (Woolf et al., 1996). As these cells produce NGP and at the same time express functional TrkA receptors on their surface (Nilsson et al., 1997), they are able to respond to NGF itself in the presence of lysophosphatidylserine (Horigome et al., 1993; Kawamoto t al., 2002). As a result, the system NGF/TrkA appears to mediate mastocyte activation through a positive feedback autocrine mechanism allowing the local amplification of the algogenic inflammatory signal. High levels of NGF are also found in neurons, where this neurotrophin is apparently responsible for the modifications of nerve fibres, associated with pain (Harpf et al. 2002). In certain forms of cancer, the excess of NGF facilitates the growth and infiltration of nerve fibres with induction of oncological pain (Zhu et al., 1999). Recent experimental studies show that, by blocking NGF, it could be possible to significantly reduce the formation of neuromas, responsible for neuropathic pain, without damaging the cell bodies of the lesioned neurons (Kryger et al., 2001). These results elicited significant interest in therapeutic approaches based on the reduction of the effects of NGF for the treatment of chronic pain (Saragovi and Gehring, 2000). In recent years, the involvement of the NGF/TrkA system in the molecular processes of pain transduction has also been demonstrated on a genetic base. In particular, mutations of the TrkA gene (localised on the chromosome 1q21-q22) are responsible for a hereditary recessive autosomic syndrome known as CIPA ("congenital insensitivity to pain with anhydrosis"), characterised by recurrent episodic fever, anhydrosis, absence of reaction to stimuli that cause pain, mental retardation and a tendency to self-mutilation (Indo et at, 1996; Saragovi and Gehring, 2000; Indo, 2001; Indo et al., 2001). Further confirmation of the involvement of NGF in the nociceptive response was recently obtained by the work on phenotype characterisation of anti-NGF transgenic mice (AD11). In these animals, the ectopic expression of the anti-NGF antibody αD11 produces a functional block of NGF in adult. This block translates in a consistent manner into an increase in the latency time of the response to harmful heat stimuli (Capsoni et al. 2000; Ruberti et al., 2000). Antibodies that are able to neutralise the biological activity of the NGF/TrkA system by blocking the ligand or the receptor may represent an important resource in pain therapy, in particular for persistent forms of pain. In this context, a very recent publication demonstrates that treatment with a neutralising anti-NGF antibody produces significant pain reduction in a murine oncological pain model (Sevcik et al., 2005). Nevertheless, in the administration protocol used by Sevcik et al, the maximum time lapse between the last injection of anti-NGF and observation of the behaviour does not exceed 4 days, so it is not a long-term effect.

A long-term effect can be defined as an effect which is still evident for at least 1-2 week(s), after the last administration of the antibody, implying that there is no necessary correlation between the effect and the bloodstream concentration of the antibody itself. A long-term effect may require new gene expression and may represent a permanent or prolonged modification of the original physiopathological state. In many cases, the drug that is capable of producing a long-term effect, may be defined as a "disease-modifying" active principle, i.e., capable of modifying in depth the course of the disease, unlike products displaying a simple pharmacological effect on the symptoms.

The authors of the present invention dispose of a panel of antibodies (directed against the NGF ligand) that are able to block the biological effects of NGF that are mediated by the TrkA ligand. Two reagents: αD11 (anti-NGF) and MNAC13 (anti-TrkA) are of particular interest. The comparison between the two antibodies, the one directed against the ligand and the other directed against the receptor, is of significant interest as the inhibition of the NGF ligand is not functionally equivalent to the inhibition of the TrkA receptor. Three points must in fact be considered:

i) stoichiometric reasons, in the context of the same system, the availability of ligand and of receptor may vary greatly and vary in a different fashion, over time;

ii) the presence of a second receptor for NGF (p75) that is shared by all the neurotrophins and mediates distinct biological functions with respect to TrkA (Hempstead, 2002);

iii) the presence, in nature, of "immature" forms of NGF (pre-pro-NGF), characterised by distinct properties, in terms of bioactivity, and binding preferably to the p75 receptor (Lee et al., 2001).

αD11 is a rat monoclonal antibody directed against mouse NGF (but also able to recognise rat and human NGF). Its interaction with NGF inhibits the binding thereof with TrkA, blocking the physiological action thereof (Cattaneo et at, 1988). αD11 also inhibits the binding of NGF to the p75 receptor. This anti-NGF antibody is absolutely unique in terms of its specificity of binding to its antigen (as compared to all the other neurotrophins), through the affinity of binding with the antigen (picomolar) and through neutralising features, showed both in vitro and in vivo (Cattaneo et al., 1988; Berardi et al., 1994; Molnar et al., 1997; Molnar et al., 1998). The alphaD11 epitope is located at the level of NGF loop I and/or NGF loop II that are exposed to the outer part of the molecule and spatially very close to each other. Moreover, the conserved reactivity of alphaD11 in different species is consistent with the epitope assignment, since amino acid residues of these two loops are highly conserved. The potent neutralising activity of alphaD11 shows that the recognised epitope is very close to the NGF receptor binding site. Moreover, the lack of cross reactivity of alphaD11 with other members of the neurotrophin family suggests that i) the epitope is located in NGF regions that are not shared with other neurotrophins, ii) the epitope itself may be involved in the "specificity path" mediating NGF-TrkA recognition. The epitope recognized by the alphaD11 antibody on the NGF molecule was identified by testing the binding activity of the antibody towards an extensive panel of NGF mutants. On the basis of this systematic screening, a region (aa. 41-49, loop 1) of the NGF molecule was identified that is highly expressed on top of NGF molecule and that is responsible (though not exclusively) for the binding of the antibody to its antigen (Gonfloni, 1995). As a matter of fact also the NGF aa. region 23-35 (loop II) may contribute to the binding.

The antibody MNAC13 is a mouse monoclonal antibody directed against the human TrkA receptor (Cattaneo et al., 1999; Pesavento et al., 2000), that is particularly effective in the inhibition of the process of TrkA activation by NGF and of downstream biological functions, both in vitro and in vivo (Cattaneo et al., 1999; Pesavento at al., 2000). The antibodies were characterized in detail from the point of view of the structure (Covaceuszach et al., 2001) and from the molecular interaction with the TrkA receptor (Covaceuszach et al., 2005).

On the basis of such in-depth knowledge around structure, by means of an innovative method, humanised versions of both αD11 and MNAC13 were generated (Hu-αD11 and Hu-MNAC13), displaying the same antigen binding features of the parental versions (patent application WO 05/061540).

The therapies that are currently available for treating pain of neuropathic origin (caused by a primary lesion or by a dysfunction of the nervous system, for example the pain associated by a lesion of the spinal cord), for treating oncological pain, and for numerous other forms of persistent pain (also of inflammatory nature) have been found to be of limited effectiveness. There is therefore an obvious need to identify and develop new molecules that have an analgesic activity and which work through a different action mechanism as compared to currently used analgesic drugs, in order to solve side effect related problems. The international patent application WO 02/20479 discloses small synthesis molecules that inhibit the TrkA receptor, having a potential analgesic activity. Nevertheless, the effect of these molecules on certain pain models has not been demonstrated. Furthermore, as compared to antibodies, the small molecules have the drawback of being more likely to penetrate the haematoencephalic barrier, with the possibility of serious side effects. In fact, the cholinergic neurons of the basal forebrain, a neuronal population that is affected by various forms of progressive neurodegeneration, including Alzheimer's disease (Saper et al., 1985), express the TrkA receptor and depend on NGF for correct functioning (Holtzman et al., 1992). The international patent application WO 01/78698 proposes the use of an NGF antagonist for preventing or treating chronic visceral pain, but not for neuropathic or oncological pain. Even if the application states that the antagonist can bind both NGF and the TrkA receptor, it is not demonstrated that, upon binding of the antagonist to the TrkA receptor, the receptor is functionally blocked. On the basis of the capacity of the two antibodies MNAC13 and αD11 to block the biological activity of NGF/TrkA, the two antibodies MNAC13 and αD11 and their respective humanised versions were tested in various (rodent) animal models of persistent pain, in particular in the model CCI ("Chronic Constriction Injury", chronic constriction injury of the sciatic nerve), one of the models available for assessment of chronic pain of a neuropathic nature (Bennett and Xie, 1988).

SUMMARY OF THE INVENTION

The object of the present invention is the use of an anti-NGF that is able to inhibit the binding between NGF and TrkA, for the preparation of a medicament for the treatment of chronic pain.

An anti-NGF molecule that blocks the biological activity of TrkA is defined as a molecule that acts as an antagonist in terms of the NGF binding with the TrkA receptor and comprises: synthetic molecule or monoclonal antibody or a biological/synthetic derivative thereof that:
  i) binds to TrkA;
  ii) inhibits the binding of NGF to the "native" TrkA receptor expressed on the surface of living cells ("native" meaning "in the natural in vivo conformation"); and
  iii) blocks the biological activity that derives from the NGF binding with the same TrkA receptor.

The term "blocking the biological activity" does not simply mean blocking activation of the receptor, defined as blocking the conversion process of the receptor itself into an "active" state but also functional neutralisation of the biological consequences that are downstream of this activation process: second messengers, new gene expression, phenotypical and functional modifications. The molecule is not only able to block TrkA in a classic in vitro test (test of neuritic growth in PC12 cells), but also in vivo (functional block of the cholinergic neurons of the basal forebrain and block of the nociception in a classic "hot plate" test).

It is an object of the invention the use of an anti-NGF antibody capable of inhibiting the binding between NGF and TrkA for the preparation of a medicament for treating and/or preventing chronic pain. Preferably the antibody is able to recognise and bind to a NGF molecule domain containing the aa. 41-49 region of human or rat NGF: EVNINNSVF (SEQ ID No. 9), more preferably the domain contains also the as 23-35 region: GDKTTATDIKGKE (SEQ ID No. 10). More preferably the antibody is capable of blocking the biological activity of TrkA.

There is also provided as an aspect of the invention a method of treatment and/or prevention of chronic pain in a subject comprising administering to the subject an effective amount of an anti-NGF antibody thereby to treat and/or prevent chronic pain in said subject. There is also provided a kit comprising a composition containing an anti-NGF antibody together with instructions directing administration of said composition to a subject in need of treatment and/or prevention of chronic pain thereby to treat and/or prevent chronic pain in said subject.

In a preferred aspect the variable region of the antibody light chain comprises at least one, more preferably two, most preferably three of the complementarity determining regions (CDRs) having the sequence selected from aa. 24 to aa. 34 of ID No. 1; from aa. 50 to aa. 56 of SEQ ID No. 1; from aa. 89 to aa. 97 of SEQ ID No. 1.

In a further preferred aspect the variable region of the antibody light chain comprises essentially the sequence of SEQ ID No. 1.

```
(VL, SEQ ID No. 1):
                            L CDR1
DIQMTQSPASLSASLGETVTIECRASEDIYNALAWYQQKPGKSPQLLIY

L  CDR2                                     L CDR3
NTDTLHTGVPSRFSGSGSGTQYSLKINSLQSEDVASYFCQHYFHYPRTF

GGGTKLELK
```

In a preferred aspect the variable region of the antibody heavy chain comprises at least one, more preferably two, most preferably three of the complementarity determining regions (CDRs) having the sequence selected from aa. 26 to aa. 35 of SEQ ID No. 2; from aa. 50 to a. 65 of SEQ ID No. 2; from aa. 98 to aa. 111 of SEQ ID No. 2.

In a further preferred aspect the variable region of the antibody heavy chain comprises essentially the sequence of SEQ ID No. 2.

```
(VH, SEQ ID NO 2):
                                  H   CDR1
QVQLKESGPGLVQPSQTLSLTCTVSGFSLTNNNVNWVRQATGRGLEWMG

H CDR2
GVWAGGATDYNSALKSRLTITRDTSKSQVFLKMHSLQSEDTATYYCAR

H CDR3
DGGYSSSTLYAMDAWGQGTTVTVSA
```

The antibody may be in single chain form and comprises a light chain variable region and a heavy chain variable region joined by a linker.

Alternatively the antibody may comprise two light chains and two heavy chains.

In a preferred aspect of the invention the anti-NGF antibody is a human or humanised antibody. The skilled in the art shall select the proper humanisation method to design the antibody, a preferred method is the method as disclosed in WO 2005/061540.

Briefly, a "humanized" variant of the antibody variable region was obtained by grafting the Complementarity Determining Regions (CDRs) of the rat antibody on to a human immunoglobulin framework. The complete structural information obtained from X-ray diffraction studies concerning the Fab fragment of the αD11 antibody was exploited to select an acceptor framework of human origin. Two different criteria were adopted to minimize structural differences between the rat αD11 and the acceptor human antibody: i) level of primary structure homology, ii) level of tridimensional structure similarity. After choosing the framework, the replacement of human residues by rat counterparts was minimized to reduce the potential immunogenicity of the resulting humanized antibody.

Exemplary humanised antibodies comprise a light chain variable region which is a humanised derivative of SEQ ID No 1 (a rat origin sequence). Exemplary humanised antibodies comprise a heavy chain variable region which is a humanised derivative of SEQ ID No 2 (a rat origin sequence).

In a preferred aspect of the invention the variable region of the humanised antibody light chain comprises essentially the sequence of SEQ ID No. 3.

```
SEQ ID NO 3 (VL, variable region of the light
chain of Hu-αD11):
                               L CDR1
DIQMTQSPSSLSASVGDRVTITCRASEDIYNALAWYQQKPGKAPKLLIY L  CDR2                                    L   CDR3
NTDTLHTGVPSRFSGSGSGTDYTLTISSLQPEDFATYFCQHYFHYPRT

FGQGTKVEIK
```

In a preferred aspect of the invention the variable region of the humanised antibody heavy chain comprises essentially the sequence of SEQ ID No. 4.

SEQ ID No. 4 (VH, variable region of the heavy
chain of Hu-αD11):
```
                       H CDR1
EVQLVESGGGLVQPGGSLRLSCAASGFSLTNNNVNWVRQAPGKGLEWV

H CDR2
GGVWAGGATDYNSALKSRFTISRDNSKNTAYLQMNSLRAEDTAVYYCA

H CDR3
RDGGYSSSTLYAMDAWGQGTLVTVSS
```

The above described humanized variable regions were cloned into appropriate expression vectors into a human IgG1 or IgG4 isotype format and transfected into mammalian cell lines to allow for expression, purification and pharmacological characterization.

Different variants of Hu-αD11 (complete IgG: heavy chain light chain) were finally produced (differing because of different constant parts).

In a preferred aspect of the invention the humanised antibody light chain has essentially the sequence of SEQ ID No. 8.

```
SEQ ID 8, Hu-αD11 Vk human Ck
DIQMTQSPSSLSASVGDRVTITCRASEDIYNALAWYQQKPGKAPKLLIY

NTDTLHTGVPSRFSGSGSGTDYTLTISSLQPEDFATYFCFQQGTKVE

IKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPV

TKSFNRGEC
(Italics = variable regions; Bold = mutations in
the rat sequence in the humanization process;
Underlined = CDRs)
```

In a preferred embodiment, the humanised anti-NGF heavy chain has essentially one of the following 3 sequences:

```
SEQ ID NO 5, Hu-antiNGF (VH) human IgG1
EVQLVESGGGLVQPGGSLRLSCAASGFSLTNNNVNWVRQAPGKGLEWV

GGVWAGGATDYNSALKSRFTISRDNSKNTAYLQMNSLRAEDTAVYYCA

RDGGYSSSTLYAMDAWGQGTLVTVSSASTKGPSVFPLAPSSKSTSGGTAA

LGCLVKDYFPEPVTVSWNSGALTSGVHTFPAVLQSSGLYSLSSVVTVPSS

SLGTQTYICNVNHKPSNTKVDKRVEPKSCDKTHTCPPCPAPELLGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSL

SLSPGK

SEQ ID NO 6, Hu-αD11 (VH) human IgG1*(IgG1
with N297A mutation, as described by Bolt et al.,
1993)
EVQLVESGGGLVQPGGSLRLSCAASGFSLTNNNVNWVRQAPGKGLEWV

GGVWAGGATDYNSALKSRFTISRDNSKNTAYLQMNSLRAEDTAVYYCA

RDGGYSSSTLYAMDAWGQGTLVTVSSASTKGPSVFPLAPSSKSTSGGTAA

LGCLVKDYFPEPVTVSWNSGALTSGVHTFPAVLQSSGLYSLSSVVTVPSS

SLGTQTYICNVNHKPSNTKVDKRVEPKSCDKTHTCPPCPAPELLGGPSVF
```

-continued
```
LFPPKPKDTLMISRTPEVTCVVVDVSHEDPEVKFNWYVDGVEVHNAKTKP

REEQYASTYRVVSVLTVLHQDWLNGKEYKCKVSNKALPAPIEKTISKAKG

QPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSL

SLSPGK

SEQ ID NO 7, Hu-αD11 (VH) human IgG4
EVQLVESGGGLVQPGGSLRLSCAASGFSLTNNNVNWVRQAPGKGLEWV

GGVWAGGATDYNSALKSRFTISRDNSKNTAYLQMNSLRAEDTAVYYCA

RDGGYSSSTLYAMDAWGQGTLVTVSSASTKGPSVFPLAPSSKSTSESTAA

LGCLVKDYFPEPVTVSWNSGALTSGVHTFPAVLQSSGLYSLSSVVTVPSS

SLGTKTYTCNVDHKPSNTKVDKRVESKYGPPCPSCPAPEFLGGPSVFLFP

PKPKDTLMISRTPEVTCVVVDVSQEDPEVQFNWYVDGVEVHNAKTKPREE

QFNSTYRVVSVLTVLHQDWLNGKEYKCKVSNKGLPSSIEKTISKAKGQPR

EPQVYTTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLSL

SLGK
(Italics = variable regions; Bold = mutations in
the rat sequence in the humanization
process; Underlined = CDRs; N297A mutation to
abolish glycosilation site).
```

In a preferred aspect the molecules of the invention are used for the preparation of a medicament for the pain of the chronic inflammatory type, preferably caused by pancreatitis, kidney stones, headaches, dysmenorrhoea, musculoskeletal pain, sprains, visceral pain, ovarian cysts, prostatitis, cystitis, interstitial cystitis, post-operative pain, migraine, trigeminal neuralgia, pain from burns and/or wounds, pain associated with trauma, neuropathic pain, pain associated with musculoskeletal diseases, rheumatoid arthritis, osteoarthritis, ankylosing spondylitis, periarticular pathologies, oncological pain, pain from bone metastases, pain from HIV.

Alternatively the pain is a neuropathic pain or an oncological pain.

According to International Association for the Study of Pain (IASP, www.iasp-pain.org <http://www.iasp-pain.org/>), pain is generally defined as "An unpleasant sensory and emotional experience associated with actual or potential tissue damage, or described in terms of such damage or both". The essential element in all forms of pain is the activation of specialized high-threshold receptors and nerve fibers to warn the organism of potential tissue damage. The involvement of inflammatory cells and processes is a common element in many pain states. The term "acute pain" means immediate, generally high threshold, pain brought about by injury such as a cut, crush, burn, or by chemical stimulation. The term "chronic pain," as used herein, means pain other than acute pain. It is understood that chronic pain often is of relatively long duration, for example, months or years and can be continuous or intermittent.

The anti-NGF antibody is suitably administered systemically. Systemic administration of the anti-NGF antibody can be performed by injection, e.g. continuous intravenous infusion, bolus intravenous infusion, subcutaneous or intramuscular injection. Alternatively other forms of administration (e.g. oral, mucosal, via inhalation, sublingually, etc.) may also be used. Local delivery of the antibody can be performed by local administration eg intra-articular injection or subcutaneous, intramuscular injection in the vicinity of affected tissues.

The anti-NGF antibody will suitably be formulated in a pharmaceutical composition appropriate for the intended route of administration. Solutions for injection will suitably contain the antibody dissolved or dispersed in an aqueous medium (eg water for injection) containing appropriate buffers and molarity modifiers eg phosphate, salt and/or dextrose.

Treatment regimen i.e. dose, timing and repetition, can be represented by single or repeated administrations (e.g. injections) of the product by the chosen administration route. The interval of dose administration can be subject to modifications depending on the extent and duration of the clinical response, as well as the particular individual and the individual clinical history. Suitably the anti-NGF antibody has a long duration of action. In particular the clinical effect of the antibody extends following administration as long as 21 days as determined from animal studies. Furthermore, preliminary data imply that anti-NGF antibodies may manifest clinical benefit for a longer period than that in which its presence can be detected in a relevant biological matrix such as serum or plasma following its administration.

In light of the intended long duration of action (i.e. an effect suitably lasting at least one week, or preferably at least two weeks eg at least three weeks or at least four weeks), suitably the antibody may be administered to subjects at a frequency of not more than once per week eg not more than once per two weeks or once per three weeks or once per four weeks.

A suitable dose of the anti-NGF antibody will typically range from 0.1 mg/kg to 10 mg/kg body weight Novel antibodies and compositions containing them disclosed herein are claimed as an aspect of the invention.

Non-limitative embodiments of the present invention will now be disclosed, with particular reference to the following figures:

FIG. 1: BIAcore analysis of the binding of the αD11 anti-NGF antibody to mouse NGF (m-NGF) and recombinant mouse proNGF (rm-proNGF). The αD111 anti-NGF antibody was immobilized on flow cell 2, while flow cell 1 was left as a blank. Each curve is obtained subtracting the background signal (measured in cell 1) to the signal measured in cell 2. The Surface Plasmon Resonance signal gives the amount of surface-bound component at each stage and is expressed in resonance units (RU).

For m-NGF binding, the immobilization of the antibody was of 3000 resonance units (RU) in the experiment of panel A and of 6000 RU in the experiment of panel B. The injected concentrations of the m-NGF are indicated on top of each curve. From a complete analysis of the data, the affinity parameters were evaluated, and resulted to be the following. $KA = 3.55 \cdot 10^{-11}$ 1/M; $KD = 2.8 \cdot 10^{-12}$ M (chi$^2$ value of 0.123).

For rm-proNGF binding (panel C), the immobilization of the antibody was of 3000 RU.

The injected concentrations of the rm-proNGF are indicated on top of each curve. A kinetic analysis of the data allowed to evaluate the following parameters: $KA = 1.2 \cdot 10^9$ 1/M; $KD = 1.9 \cdot 10^{-9}$ M (chi$^2$ value of 0.09).

Figure 2:
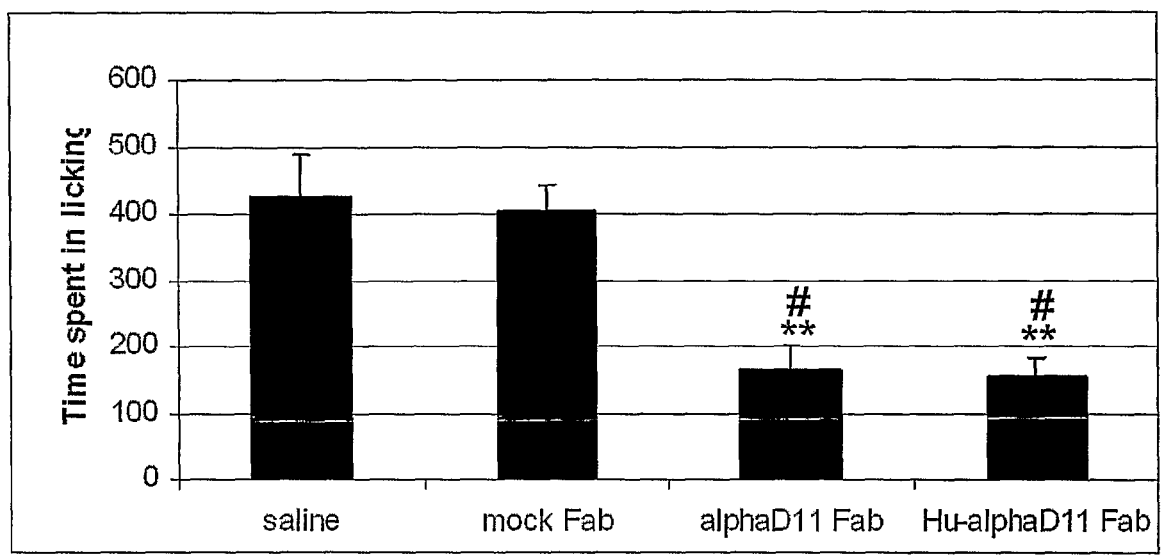

FIG. 2: Effect of Fab aD11 (alphaD11) and Fab Hu-aD11 (Hu-alphaD11) anti-NGF antibodies on the formalin-evoked pain (phase 2 of the formalin test: 15-40 min. Phase 2 corresponds to inflammation-related pain). Mice were subcutaneously injected with 5% formalin in the dorsal portion of the right hindpaw.

Treatment consisted in antibody injection (Fab alphaD11 or Fab Hu-alphaD11 vs either mock Fab or saline) performed (in the same paw as for formalin) 45 min, before formalin injection and testing (single dose of each antibody: 12.5 μg). Each experimental group included at least 8 animals. Statistical analysis of data showed a significant analgesic effect of anti-NGF treatment (both for the parental and the humanized version of the antibody) that was clearly specific for the second phase (inflammatory) of pain response (time spent in licking): The effect of anti-NGF antibodies (both parental and humanized versions) is statistically different (ANOVA) with respect to either saline (** $p<0.01$) or mock Fab treatment (#$p<0.05$).

Figure 3:
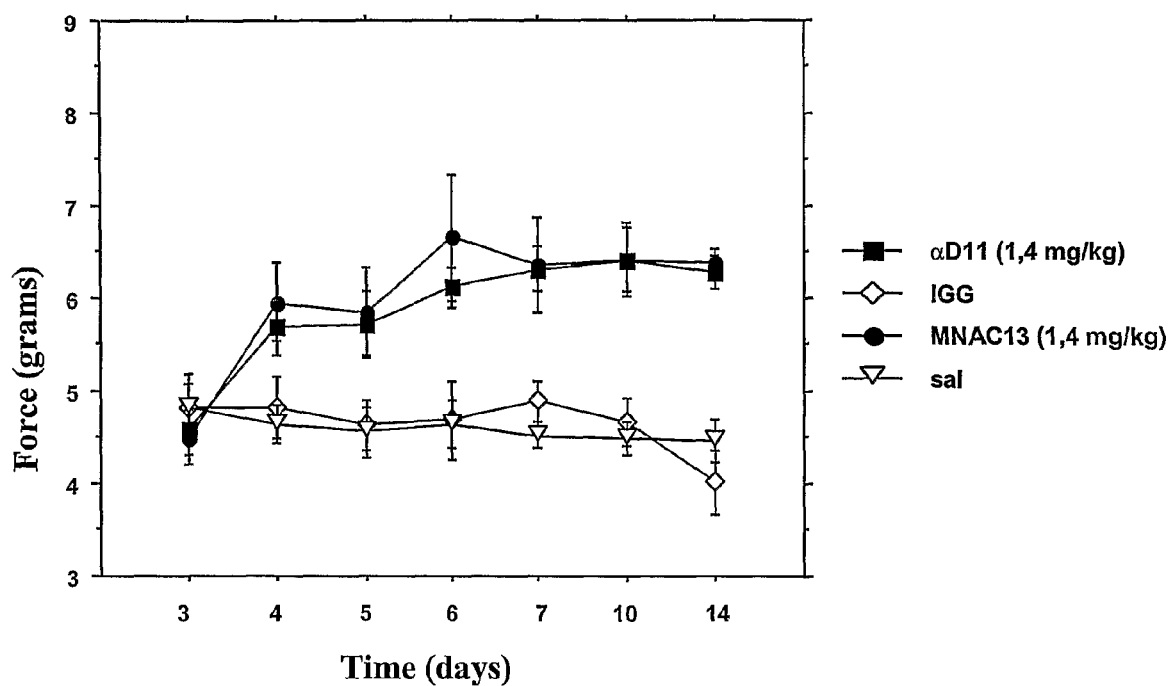

FIG. 3: Effect of the anti-TrkA monoclonal antibody MNAC13 (1.4 mg/kg) and anti-NGF monoclonal antibody αD11 (1.4 mg/kg) on neuropathic pain: mechanical allodynia measured by means of a plantar dynamic aesthesiometer; CD1 mice subjected to chronic constriction of the sciatic nerve; the antibodies are injected I.P. at days 3, 4, 5, 6 after lesion of the sciatic nerve. Observation period: from day 3 to day 14. As a negative control, both saline (sal) and mouse immunoglobulins (IgG, 1.4 mg/kg) were used. Results were expressed in terms of absolute value (grams) of the threshold force for the hindpaw ipsilateral to lesion. The values were subjected to statistical analysis by means of an analysis of the variance (ANOVA) for repeated measurements, in which both the "treatment" factor and the repeated measurement (days) were significant with $p<0.01$. The animals treated with anti-TrkA or anti-NGF are significantly different from the controls from day 4 to day 14.

Figure 4:
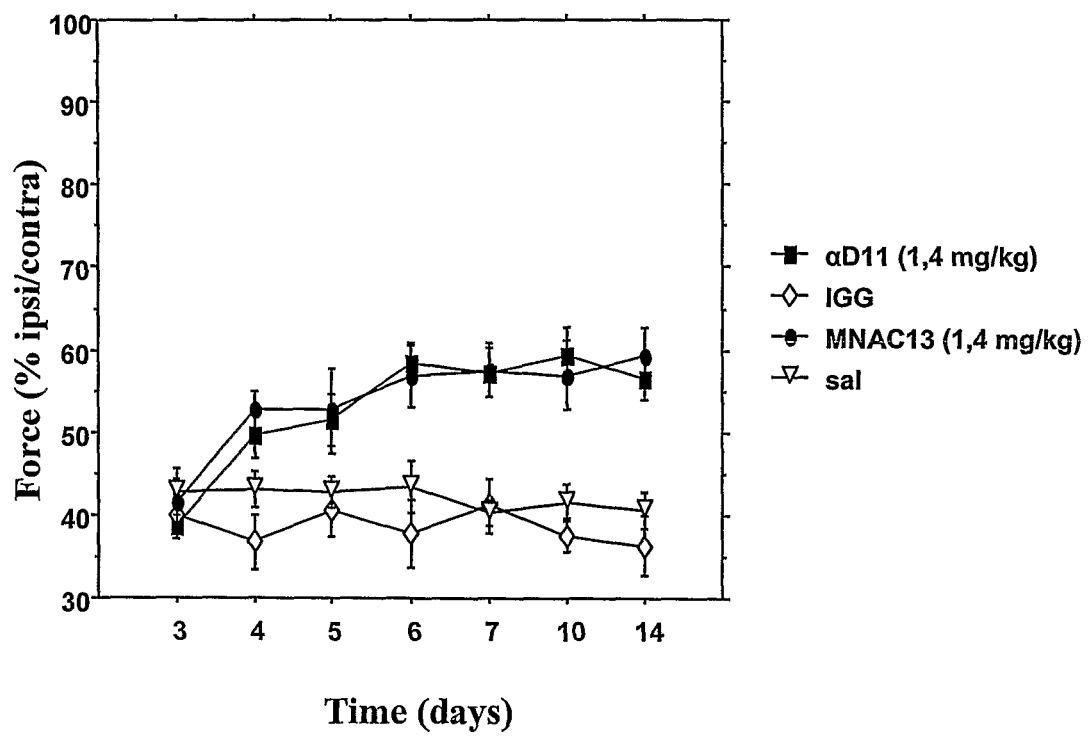

FIG. 4: Effect of the anti-TrkA monoclonal antibody MNAC13 (1.4 mg/kg) and anti-NGF αD11 antibody (1.4 mg/kg) on neuropathic pain: mechanical allodynia measured by means of a plantar dynamic aesthesiometer; CD1 mice subjected to chronic constriction of the sciatic nerve; the antibodies were injected I.P. at days 3, 4, 5, 6 after lesion of the sciatic nerve. Observation period: from day 3 to day 14. As a control, both saline (sal) and mouse immunoglobulins (IgG, 1.4 mg/kg) were used. Results were expressed as a percentage, % (ratio between the threshold force of the hindpaw ipsilateral to lesion and that corresponding to the contralateral hindpaw). The corresponding absolute values were subjected to statistical analysis by means of an analysis of the variance (ANOVA) for repeated measurements, in which both the "treatment" factor and the repeated measurement (days) were significant with $p<0.01$ (at least). The animals treated with anti-TrkA o anti-NGF were significantly different from the controls from day 4 to day 14.

Figure 5:
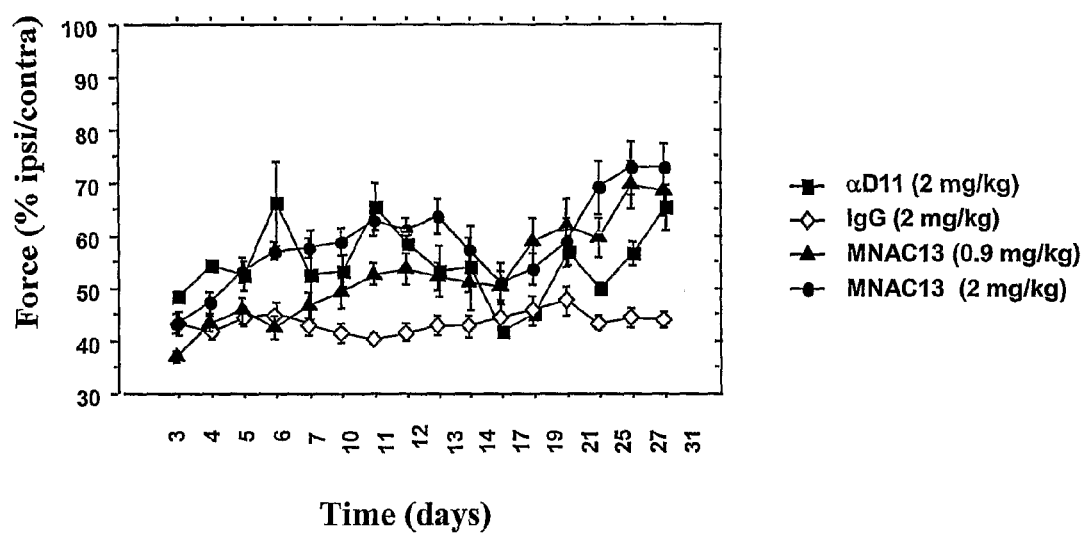

FIG. 5: Comparison between the effects of the anti-TrkA monoclonal antibody MNAC13 (2 doses: 0.9 and 2 mg/kg) and those of the anti-NGF monoclonal antibody αD11 (2 mg/kg dose), on neuropathic pain: mechanical allodynia measured by means of a plantar dynamic aesthesiometer, CD1 mice subjected to chronic constriction of the sciatic nerve; the antibodies were injected I.P. at days 3, 4, 5, 6, 7, 8, 9, 10 after lesion of the sciatic nerve. Observation period: from day 3 to day 31. As a negative control, mouse immunoglobulins were used (IgG, 2 mg/kg). Results were expressed as a percentage % (ratio between the threshold force of the hindpaw ipsilateral to lesion and that corresponding to the contralateral hindpaw). The corresponding absolute values were subjected to statistical analysis by means of an analysis of the variance (ANOVA) for repeated measurements, in which both the "treatment" factor and the repeated measurement (days) were significant with $p<0.01$ (at least). The animals treated with MNAC13 were significantly different from the controls up to the last day of observation (31), from day 5 (greater dose of MNAC13) or from day 7 (lesser dose of MNAC13). The animals treated with αD11 were significantly different from the controls up to the last day of observation (31), from day 4 to day 14, and from day 21 to day 31.

Figure 6:
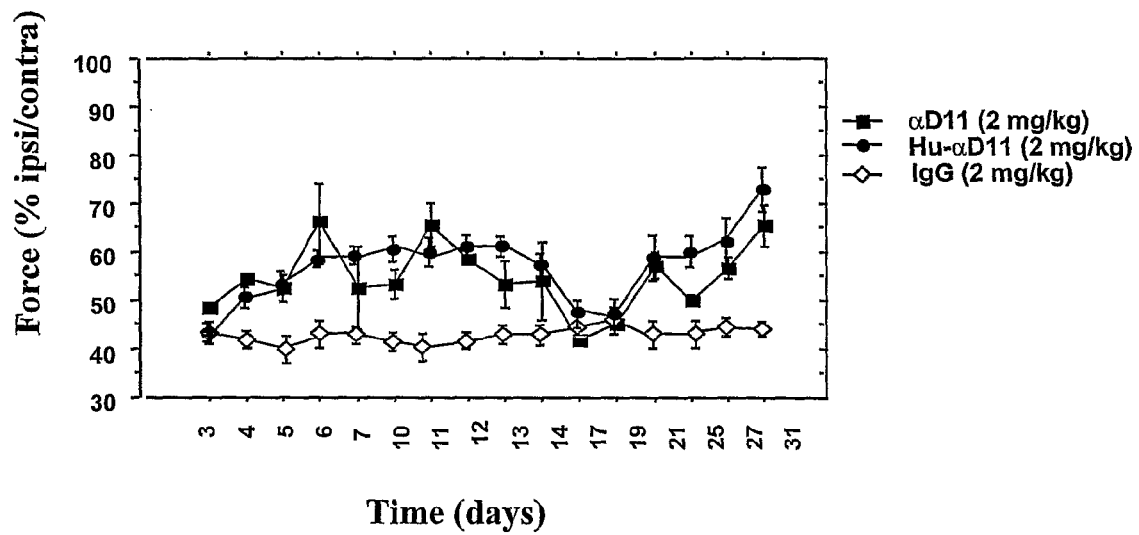

FIG. 6: Comparison between the effects of the parental (αD11) and humanized (Hu-αD11, human IgG4 format) version of the anti-NGF neutralizing antibody (1 dose tested: 2 mg/Kg) on neuropathic pain: mechano-allodynia measured by means of dynamic plantar aestesiometer, CD1 mice subject to CCI (chronic constriction injury) of the sciatic nerve; antibodies I.P. injected at days 3, 4, 5, 6, 7, 8, 9, 10, following lesion of the sciatic nerve. Observation period: from day 3 to day 31. Rat Immunoglobulins were employed for negative control (IgG, 2 mg/kg). Results expressed as % (ratio between the threshold force for the hindpaw ipsilateral to lesion and the contralateral hindpaw). Analysis of variance (ANOVA) for repeated measures on corresponding absolute values in which both the factor "treatment" and the repeated measure (days) were significant with (at least) $p<0.01$. Animals treated with either αD11 or Hu-αD11 were significantly different from controls up to the last observation day (31), from day 4 to day 14, as well as from day 21 up to day 31.

METHODS

Production of Monoclonal Antibodies

The monoclonal antibodies MNAC13 and αD11 are produced from a hybridoma supernatant, according to standard methods, disclosed above (Galfre and Milstein, 1981; Cattaneo et al., 1988; Cattaneo et al., 1999). The supernatant containing each antibody was subjected to precipitation (29% ammonium sulphate), followed by dialysis against PBS 1× (Spectra-Por 12/14K membrane, Spectrum) and affinity chromatography on sepharose protein G column (4-Past Flow, Amersham Biosciences). Elution occurred by means of a low pH (HCl 5 mM) solution that was neutralised upon collection. The final eluate was concentrated (Amicon Ultra-15, 50K, Millipore) to obtain preparations of purified antibody in concentrations between 1 and 5 mg/ml.

The Fab (Fragments Antigen binding) version of the αD11 antibody was produced as previously described (patent application WO 05/061540, Covaceuszach et al., 2004). Briefly, Fab fragments were obtained from the correspondent whole monoclonal antibodies (IgG format) by papain proteolysis, followed by a ion exchange chromatography purification step and concentration of the Fab fragments collected in the flow-through. In order to separate the Fab fragments from the quite low amount of uncleaved IgG that was still present, size exclusion chromatography on a Superdex G75 column (Pharmacia) was performed using an FPLC system (Pharmacia), followed by a final concentration step.

As far as the humanised versions (IgG1/IgG1*/IgG4) of the 2 antibodies (Hu-αD11 and Hu-MNAC13) are concerned, they were also purified as disclosed above, starting from the supernatants of stably transfected cell lines, which were stable cotransfectants for the heavy chain (pVH/CMVexpress) and the light chain (pVL/CMVexpress) of each antibody. The vectors used have been disclosed previously (patent application WO 05/061540). The stable co-transfected clones were obtained through double selection with G418 and mycophenolic acid. In order to produce the IgG4 variant of Hu-αD11, since the pVH/CMVexpress vector comprises the constant part of human IgG1, this was replaced by the corresponding Fc region of IgG4 (cloned by RT-PCR from human lymphocyte RNA). The IgG1* variant (=IgG11 with the N297A mutation described by Bolt et al., 1993) was generated by site directed mutagenesis.

Surface Plasmon Resonance Studies

Experiments were performed on CM5 chips with amine coupling, using a BIAcore 2000 machine. Coupling was performed with a specific kit purchased at BIAcore and the coupling reaction was carried out according to manufacturer's instructions.

Anti-NGF antibodies were immobilized on chip, while mouse NGF (m-NGF, Alomone) or recombinant mouse proNGF (rm-proNGF) were injected at decreasing concentrations to obtain binding curves.

The flow used in the experiments was of 30 μl/min, unless otherwise indicated. The regeneration of the chip was carried out in all cases with a pulse (10 μL) of 10 mM Glycine pH 1.5, Data collected were analyzed using the Package BIAevaluation 3.0. The apparent equilibrium constant $K_D$ is defined as the $k_e/k_d$ ratio.

Experiments in Murine Pain Models

The animals were treated and handled in accordance with the guidelines of the IASP Ethical Committee and the Italian national law (DL116/92, application of European Direction 86/609/EEC) on the use of animals in research. Every necessary effort was made to minimise the suffering of the animals and to use the minimum amount of animals required to produce reliable scientific data.

Formalin Test

For the preliminary formalin tests (Porro and Cavazzuti, 1993), CD1 male mice (Charles River Labs, Como, Italy) were used, weighing 35-40 g at the beginning of the experiments. Upon their arrival in the laboratory (at least 2 weeks before the experiments), mice were housed in standard transparent plastic cage (4 for cage) at constant temperature (22±1° C.) and relative humidity (60%), under a regular light/dark schedule (light 7.00-19.00). Food and water were unlimited. The experiments were carried out between 09.00 and 14.00 hours. For the formalin test, one animal at a time was placed in a transparent plexiglass cage (30×12×13 cm), and allowed to move freely for 30 min before the beginning of the test. After this adaptation period, 20 μl of formalin solution (5% in saline) were subcutaneously (so) injected into the dorsal surface of the right hind paw of mice using a microsyringe equipped with a 26-gauge needle and the observation period started. A mirror was placed behind the cage and a videocamera in front of the cage to allow an unimpeded view of the animal's hind-paws. The licking activity, i.e. the total amount of time the animal spent licking and/or biting the injected paw, was taken as index of pain. The licking activity was recorded continuously for 40 min and calculated in blocks of consecutive 5-min periods (phase 2 corresponds to the block 15-40 min and can be identified with inflammation-related pain). In addition, to assess the effects of formalin injection on the spontaneous behaviours, general activity (time spent exploring the environment during walking, rearing and leaning), and self-grooming (time spent for face and body cleaning) during the formalin test were also continuously recorded for 40 min. No significant differences following treatment with anti-NGF antibodies were observed for these parameters. In this set of experiments, antibodies were administered as Fabs (fragments antigen binding; single dose of each antibody: 12.5 μg per animal).

Each mouse was subcutaneously (sc) injected 45 min before the test with anti-NGF antibody (either parental or humanized) or irrelevant Fab into the dorsal surface of the right hind paw using a Hamilton micro-syringe with a 26-gauge needle (volume injected=20 μl). Each animal underwent only one treatment. Testing was performed blind as for treatment group to which each subject belonged. The two phases characterizing the formalin test were separately analysed by one-way ANOVAs.

Sciatic Nerve Surgery

Male CD1 mice, weighing approximately 35 g, were anaesthetised (intraperitoneal injection with 500 mg/kg chloral hydrate), the sciatic nerve of the right hind leg was exposed to undergo loose ligature by means of stitching thread according to the chronic constriction lesion model (CCI) of the sciatic nerve, disclosed by Bennett and Xie (1988). The loose ligature of the sciatic nerve, at level of the upper thigh, induced peripheral mononeuropathy characterised by thermal/mechanical allodynia and hyperalgesia. By ligation of the nerve at 3 different but near points, the neuropathy was fully developed 3 days following the lesion and lasted for 2-3 months.

Pharmacological Treatment

Starting from the third day following the lesion, anti-NGF ($\alpha$D11) blocking antibodies or anti-TrkA (MNAC13) antibodies were administered in an entire form (Mab) that were diluted in saline solution (vehicle), as indicated in Table I. As controls, mouse or rat irrelevant immunoglobulins used (IgG), in the same dose as the blocking antibodies (at the greater dose if 2 doses were used), or saline solution. Each experimental group included N=10 animals (unless explicitly stated otherwise).

TABLE I

Administration protocols and measurement of mechanical allodynia.

| Antibody | Dose | Administration i.p. | Allodynia measurement |
|---|---|---|---|
| MNAC 13 $\alpha$D11 | 50 µg/mouse = 1.4 mg/kg | 4, at days 3, 4, 5, 6 after lesion | Days 3 to 14 |
| MNAC 13 $\alpha$D11 | 70 µg/mouse = 2 mg/kg | 8, at days 3, 4, 5, 6, 7, 8, 9, 10 after lesion | Days 3 to 31 |
| MNAC 13 | 30 µg/mouse = 0.9 mg/kg | | |

Mechanical allodynia was measured by means of a plantar dynamic aesthesiometer (Ugo Basile), as indicated in Table I. Day 3 was considered the baseline.

The same protocols were used to assess the analgesic action of the humanised versions of the two antibodies MNAC13 and $\alpha$D11.

Statistical Analysis of Results (CCI Experiments)

The results were expressed in 2 different ways, both as an absolute value of the threshold force value (in grams) that was sufficient for the animal to retract the hind leg that is ipsilateral to the lesion, or in percentage value, as the ratio between the absolute values of the hind legs (ipsilateral/contralateral). The values were subjected to statistical analysis by means of an analysis of the variance (ANOVA) for repeated measurements, in which both the "treatment" factor and the repeated measurement (days) were significant with $p<0.01$.

Results

Binding

A BIACORE study was performed, aimed at further characterising the binding properties of the $\alpha$D11 anti-NGF antibody (and its humanized variant) by evaluating the binding affinity of this antibody for mouse NGF and recombinant mouse pro-NGF. FIG. 1 shows the results of these experiments: the $\alpha$D11 antibody binds with different kinetics on NGF and proNGF. Similar results were also obtained with Hu-$\alpha$D11.

The very small dissociation constant from NGF is representative of a very tight binding of the antibody to its antigen, and is quite a unique example among antibodies binding kinetics. By comparing the anti-NGF antibody binding to NGF and to proNGF, it is possible to assess that, in the latter case, the affinity is almost three orders of magnitude lower (nanomolar instead of picomolar). Considering that proNGF differs from NGF only by a short stretch of additional amino acids, this difference in binding affinities is absolutely unexpected and surprising.

As proNGF preferably binds to p75 (Lee, 2001), whereas mature NGF has a higher affinity for the TrkA receptor, $\alpha$D11 and Hu$\alpha$D11 can be considered as novel selective inhibitors of the TrkA-mediated pathway, a remarkable property that has a particular relevance in view of the clinical use of anti-NGF neutralizing antibodies.

Inflammatory Pain

A first set of in vivo experiments, performed in mice and concerning formalin-evoked pain (inflammatory pain), demonstrated that:

(i) the $\alpha$D11 anti-NGF antibody (in Fab format) was able to significantly reduce the pain response (formalin test: phase 2), as compared to an irrelevant Fab;

(ii) the same result could be obtained by replacing $\alpha$D11 with its humanized variant (Hu-$\alpha$D11, FIG. 2).

This means that Hu-$\alpha$D11 displays as powerful analgesic properties as $\alpha$D11 in a relevant model of inflammatory pain.

Neuropathic Pain

The results on the CCI model showed that the two blocking antibodies MNAC13 and $\alpha$D11 (FIG. 3 and FIG. 4) had a significant analgesic effect. In particular, a similar result was observed for the two antibodies at the 1.4 mg/kg dose. As shown in FIG. 3 and FIG. 4, they started to have an analgesic effect from the second day of administration (day 4), reaching the maximum effect around day 6, keeping substantially the same analgesic efficacy for the entire duration of the observation until day 14. Expressing the result in percentage terms (ratio between the threshold force of the hindpaw ipsilateral to lesion and that corresponding to the contralateral hindpaw), as in FIG. 4, it can be stated that for each of the two blocking antibodies, the maximum percentage value was around 60%, being around 40% for the control groups (IgG and saline).

When the animals were observed for 4 weeks, up to day 31, administration of the antibodies blocking the NGF-TrkA system (FIG. 5 and FIG. 6) revealed a two-phase effect. The first phase of analgesic efficacy (from day 3 to day 17, i.e. until a week after the last injection) was characterised by a maximum effect around days 11-12. After a reduction of the effect (up to day 17), a second analgesic phase was observed with an increase in the effect up to day 31. Two phases in the analgesic action of NGF/TrkA blocking antibodies can therefore be distinguished: the first ("pharmacological" effect), that comprises the treatment period and the first week after the last injection of antibody (the week during which the effect diminishes, parallel to the haematic concentration of the antibody); the second, which identifies a long-term effect, probably requiring new genic expression, which is an effect that gives these antibodies the unique feature Cm the field of neuropathic pain) of being a "disease-modifying" active principle, i.e. capable of modifying in depth the course of the disease, unlike the products currently used in this therapeutical context, which demonstrate a simple pharmacological effect on the symptoms. In FIG. 5, the analgesic effect of the 2 doses of MNAC13 anti-TrkA (2 and 0.9 mg/Kg) was compared with that of $\alpha$D11 (2 mg/kg).

The results are expressed in percentage terms. The temporal profile of αD11 efficacy is similar to that of MNAC13, although, at day 17, the animals treated with αD11 were indistinguishable from the controls (IgG), whilst all those treated with MNAC13 still differed significantly (p<0.01). From day 21 αD11 recovered analgesic effect, which reached a final level (day 31) that was similar to that of MNAC13 (greater than 60%, as compared to 40% of controls).

Substantially identical results to those illustrated above were obtained when instead of the αD11 antibody, the variants of its humanised version (Hu-αD11) were employed (dose used: 2 mg/kg for each antibody), confirming that the latter have the same analgesic properties as the parental version. The antibody was humanised with the method of WO2005/061540, both at the light (SEQ ID No. 3) and the heavy chain (SEQ ID No. 4) variable regions. To construct whole humanised antibodies, different constant regions were utilised, as above described (SEQ ID No. 5-8).

As typical example of the equivalence in terms of analgesic activity (CCI) of parental and humanized antibodies, FIG. 6 shows the comparison between αD11 and Hu-αD11 (IgG4 format).

On this basis, it is possible to state that Hu-αD11 has the same long-term effect as its parental version.

BIBLIOGRAPHY

Bennett G J, Xie Y K (1988). Pain 33:87-107.
Berardi N, Cellerino A, Domenici L, Fagiolini M, Pizzorusso T, Cattaneo A, Maffei L (1994) Proc Natl Acad Sci USA 91:684-688.
Bolt S, Routledge E, Lloyd I, Chatenoud L, Pope H, Gorman S D, Clark M, Waldmann H (1993) Bur J Immunol 23: 403-411.
Burnstock G (2001) Trends Pharmacol Sci 22:182-188.
Capsoni S, Ugolini G, Comparini A, Ruberti F, Berardi N, Cattaneo A (2000) Proc Natl Acad Sci USA 97:6826-6831.
Cattaneo A, Rapposelli B, Calissano P (1988) J Neurochem 50:1003-1010.
Cattaneo A, Capsoni S, Margotti E, Rigbi M, Kontsekova B, Pavlik P, Filipcik P, Novak M (1999) J Neurosci 19:9687-9697.
Chuang H H, Prescott E D, Kong H, Shields S, Jordt S E, Basbaum A I, Chao M V, Julius D (2001) Nature 411: 957-962,
Covaceuszach S, Cattaneo A, Lamba D (2001) Acta Crystallogr D Biol Crystallogr 57:1307-1309.
Covaceunzach S, Cassetta, A., Cattaneo A, Lamba D (2004) Acta Crystallogr D Biol Crystallogr 60:1323-1327.
Covaceuszach S, Cattaneo A, Lamba D (2005) Proteins 58:717-727.
Djouhri L, Dawbarn D, Robertson A, Newton R, Lawson S N (2001) J Neurosci 21:8722-8733.
Frade J M, Barde Y A (1998) Bioessays 20:137-145.
Galfre G, Milstein C (1981) Methods Enzymol 73:3-46.
Gonfloni S (1995) Recombinant antibodies as structural probes for neurotrophins. SISSA PhD Thesis.
Harpf C, Dabernig J, Humpel C (2002) Muscle Nerve 25:612-615.
Hempstead B L (2002) Curr Opin Neurobiol 12:260-267.
Holtzman D M, Li Y, Parada L F, Kinsman S, Chen C K, Valletta J S, Zhou J, Long J B,
Mobley W C (1992) Neuron 9:465-478.
Horigomne K, Pryor I C, Bullock E D, Johnson E M, Jr. (1993) J Biol Chem 268:14881-14887.
Hunt S P, Mantyh P W (2001) Nat Rev Neurosci 2:83-91.
Indo Y (2001) Hum Mutat 18:462-471.
Indo Y, Tsuruta M, Hayashida Y, Karim M A, Ohta K, Kawano T, Mitsubuchi H,
Tonoki H, Awaya Y, Matsuda I (1996) Nat Genet 13:485-488.
Indo Y, Mardy S, Miura Y, Moosa A, Ismail B A, Toscano E, Andria G, Pavone V,
Brown D L, Brooks A, Endo F, Matsuda I (2001) Hum Mutat 18:308-318.
Julius D, Basbaum A I (2001) Nature 413:203-210.
Kaplan D R (1998) Prog Brain Res 117:35-46.
Kawamoto K, Aoki J, Tanaka A, Itakura A, Hosono H, Arai H, Kiso Y, Matsuda H (2002) J Immunol 168:6412-6419.
Khakh B S (2001) Nat Rev Neurosci 2:165-174.
Kryger G S, Kryger Z, Zhang F, Shelton D L, Lineaweaver W C, Buncke H I J (2001) J Hand Surg [Am] 26:635-644.
Lee R, Kermani P, Teng K K, Hempstead B L (2001) Science 294:1945-1948.
Levi-Montalcini R (1987) Science 237:1154-1162.
Levi-Montalcini R, Skaper S D, Dal Toso R, Petrelli L, Leon A (1996) Trends Neurosci 19:514-520.
Levine J D (1998) Neuron 20:649-654.
Molnar M, Ruberti F, Cozzari C, Domenici L, Cattaneo A (1997) Neuroreport 8:575-579.
Molnar M, Tongiorgi E, Avignone E, Gonfloni S, Ruberti F, Domenici L, Cattaneo A (1998) Eur J Neurosci 10:3127-3140.
Morisset V, Ahluwalia J, Nagy I, Urban L (2001) Eur J Pharmacol 429:93-100.
Nakatsuka T, Fitrue H, Yosbimura M, Gn J G (2002) J Neurosci 22:1228-1237.
Nilsson G, Forsberg-Nilsson K, Xiang Z, Hallbook F, Nilsson K, Metcalfe D D (1997) Eur J Immunol 27:2295-2301.
Porro C A, Cavazzuti M (1993) Spatial and temporal aspects of spinal cord and brainstem activation in the formalin pain model. Prog Neurobiol 41: 565-607.
Pesavento E, Margotti E, Righi M, Cattaneo A, Domenici L (2000) Neuron 25:165-175.
Ruberti F, Capsoni S, Comparini A, Di Daniel E, Franzot J, Gonfloni S, Rossi G,
Berardi N, Cattaneo A (2000) J Neurosci 20:2589-2601.
Saper C B, German D C, White C L, 3rd (1985) Neurology 35:1089-1095.
Saragovi H U, Gehring K (2000) Trends Pharmacol Sci 21:93-98.
Sevcik M A, Ghilardi J R, Peters C M, Lindsay T H, Halvorson K G, Jonas B M, Kubota K,
Kuskowski M A, Boustany L, Shelton D L, Mantyh P W (2005) Pain 115:128-141.
Shu X, Mendell L M (1999) Neurosci Lett 274:159-162.
Sivilotti L, Nistri A (1991) Prog Neurobiol 36:35-92.
Woolf C J, Ma Q P, Allchome A, Poole S (1996) J Neurosci 16:2716-2723.
Zhu Z, Friess H, diMola F F, Zimmermann A, Graber H U, Kore M, Buchler M W (1999) J Clin Oncol 17:2419-2428.

INCORPORATION OF SEQUENCE LISTING

Incorporated herein by reference in its entirety is the Sequence Listing for the application. The Sequence Listing is disclosed on a computer-readable ASCII text file titled, "sequence_listing.txt", created on Mar. 5, 2009. The sequence_listing.txt file is 18.7 kb in size.

The invention claimed is:

1. A method of treatment of chronic pain in a subject comprising administering to the subject an effective amount of an anti-NGF antibody capable of inhibiting binding NGF and TrkA to treat chronic pain in said subject, wherein (a) the variable region of the antibody light chain comprises three complementarity determining regions (CDRs) having the sequences of from amino acid 24 to amino acid 34 of SEQ ID NO. 1; from amino acid 50 to amino acid 56 of SEQ ID NO. 1; and from amino acid 89 to amino acid 97 of SEQ ID NO. 1; and (b) the variable region of the antibody heavy chain comprises three of the complementarity determining regions (CDRs) having the sequences of amino acid 26 to amino acid 35 of SEQ ID NO. 2; from amino acid 50 to amino acid 65 of SEQ ID NO. 2; and from amino acid 98 to amino acid 111 of SEQ ID NO. 2.

2. The method of claim 1 wherein the antibody blocks the biological activity of TrkA.

3. The method of claim 1 wherein the variable region of the antibody light chain comprises the sequence of SEQ ID No. 1.

4. The method of claim 1 wherein the variable region of the antibody heavy chain comprises the sequence of SEQ ID No. 2.

5. The method of claim 1 wherein the antibody is in single chain form and comprises a light chain variable region and a heavy chain variable region joined by a linker.

6. The method of claim 1 wherein the antibody comprises two light chains and two heavy chains.

7. The method of claim 1 wherein the anti-NGF antibody is a humanized antibody.

8. The method of claim 7 wherein the variable region of the humanized antibody light chain comprises the sequence of SEQ ID No. 3.

9. The method of claim 7 wherein the variable region of the humanized antibody heavy chain comprises the sequence of SEQ ID No. 4.

10. The method of claim 7 wherein the humanized antibody light chain has the sequence of SEQ ID NO. 8.

11. The method of claim 7 wherein the humanized antibody heavy chain has a sequence selected from SEQ ID No. 5, SEQ ID No. 6, SEQ ID No. 7.

12. The method of claim 1 wherein the chronic pain is of the chronic inflammatory type.

13. The method of claim 12 wherein the chronic pain is caused by pancreatitis, kidney stones, headaches, dysmenorrhea, musculoskeletal pain, sprains, visceral pain, ovarian cysts, prostatitis, cystitis, interstitial cystitis, post-operative pain, migraine, trigeminal neuralgia, pain from burns and/or wounds, pain associated with trauma, neuropathic pain, pain associated with musculoskeletal diseases, rheumatoid arthritis, osteoarthritis, ankylosing spondylitis, periarticular pathologies, oncological pain, pain from bone metastases, pain from HIV.

14. The method of claim 1 wherein the pain is neuropathic pain.

15. The method of claim 1 wherein the pain is oncological pain.

16. The method of claim 1 wherein the antibody has a long duration of action.

17. The method of claim 1, wherein said antibody is administered at a frequency of not more than once per week.

18. The method of claim 1, wherein said antibody is a rat IgG1 isotype antibody.

19. The method of claim 1, wherein said antibody is an IgG4 isotype antibody.

20. The method of claim 1, wherein the variable region of the humanized antibody light chain comprises the sequence of SEQ ID NO: 3, the variable region of the humanized antibody heavy chain comprises the sequence of SEQ ID NO: 4, and the antibody is an IgG4 isotype antibody.

* * * * *